United States Patent
Breiter et al.

(10) Patent No.: US 9,408,964 B2
(45) Date of Patent: Aug. 9, 2016

(54) POWER INJECTION CATHETERS AND METHOD OF INJECTING

(75) Inventors: Catherine C. Breiter, Holladay, UT (US); Jordan P. Diamond, Salt Lake City, UT (US)

(73) Assignee: C. R. Bard, Inc., Murray Hills, NJ (US)

( * ) Notice: Subject to any disclaimer, the term of this patent is extended or adjusted under 35 U.S.C. 154(b) by 2036 days.

(21) Appl. No.: 11/321,182

(22) Filed: Dec. 29, 2005

(65) Prior Publication Data

US 2006/0149214 A1    Jul. 6, 2006

Related U.S. Application Data

(63) Continuation-in-part of application No. 11/029,299, filed on Jan. 4, 2005, now Pat. No. 7,931,619.

(51) Int. Cl.
| | | |
|---|---|---|
| *A61M 5/142* | (2006.01) | |
| *A61M 5/00* | (2006.01) | |
| *A61M 5/168* | (2006.01) | |
| *A61M 5/14* | (2006.01) | |

(52) U.S. Cl.
CPC ........... *A61M 5/007* (2013.01); *A61M 5/16854* (2013.01); *A61M 5/1408* (2013.01); *A61M 2205/3355* (2013.01)

(58) Field of Classification Search
CPC .......... A61M 2039/242; A61M 5/007; A61M 5/1408; A61M 5/16854
USPC .............................. 604/27, 29–35, 43–45, 173, 604/167.01–167.06
See application file for complete search history.

(56) References Cited

U.S. PATENT DOCUMENTS

| | | | |
|---|---|---|---|
| 3,543,759 A | 12/1970 | McWhorter | |
| 3,610,226 A | 10/1971 | Albisser et al. | |

(Continued)

FOREIGN PATENT DOCUMENTS

| | | |
|---|---|---|
| WO | 9722374 A1 | 6/1997 |
| WO | 9916498 A1 | 4/1999 |

OTHER PUBLICATIONS

Edward G. Walsh et al., "Effect of Contrast Agent Viscosity and Injection Flow Velocity on Bolus Injection Pressures for Peripheral Venous Injection in First-Pass Myocardial Perfusion Studies." Technology and Health Care 10 (2002) ISO Press. pp. 57-63.

(Continued)

*Primary Examiner* — Aarti B Berdichevsky
(74) *Attorney, Agent, or Firm* — Rutan & Tucker, LLP

(57) ABSTRACT

Power injection catheters for high flow rate delivery of fluids are disclosed. In one embodiment, a catheter may include a body defining one lumen and a plurality of extension tubes each comprising a lumen in fluid communication with the one lumen of the catheter body. Further, an extension tube may be configured for performing power injection and an extension tube may include a proximal valve. In another embodiment, a catheter may comprise a plurality of lumens and extension tubes, each of the extension tubes comprising a lumen in fluid communication with one lumen of the catheter body, respectively. At least one extension tube may be configured for performing power injection and at least one extension tube may include a proximal valve. Such catheters may include a pressure relief mechanism for preventing overpressurizing of the catheter. A method of injecting a fluid into a patient's body is disclosed.

21 Claims, 14 Drawing Sheets

(56) References Cited

U.S. PATENT DOCUMENTS

| | | | |
|---|---|---|---|
| 3,677,243 A | 7/1972 | Nerz | 604/161 |
| 3,921,631 A | 11/1975 | Thompson | 604/508 |
| 4,000,741 A | 1/1977 | Binard et al. | |
| 4,044,793 A | 8/1977 | Krueger et al. | |
| 4,099,528 A | 7/1978 | Sorenson et al. | |
| 4,123,091 A | 10/1978 | Cosentino et al. | |
| 4,240,430 A | 12/1980 | Binard et al. | |
| 4,403,988 A | 9/1983 | Binard et al. | |
| 4,439,182 A | 3/1984 | Huang | |
| 4,451,256 A | 5/1984 | Weikl et al. | 604/164.03 |
| 4,471,778 A | 9/1984 | Toye | |
| 4,493,696 A | 1/1985 | Uldall et al. | |
| 4,502,502 A | 3/1985 | Krug | |
| 4,563,180 A | 1/1986 | Jervis et al. | 604/523 |
| 4,588,402 A | 5/1986 | Igari et al. | |
| 4,592,749 A | 6/1986 | Ebling et al. | |
| 4,671,786 A | 6/1987 | Krug | |
| 4,722,725 A | 2/1988 | Sawyer et al. | |
| 4,787,886 A | 11/1988 | Cosman | |
| 4,795,431 A | 1/1989 | Walling | |
| 4,883,459 A | 11/1989 | Calderon | |
| 4,967,703 A | 11/1990 | Donnez | |
| 4,969,879 A | 11/1990 | Lichte | |
| 4,976,703 A | 12/1990 | Franetzki et al. | 604/247 |
| 5,053,004 A | 10/1991 | Markel et al. | |
| 5,129,887 A | 7/1992 | Euteneuer et al. | |
| 5,149,330 A | 9/1992 | Brightbill | |
| 5,152,298 A | 10/1992 | Kreyenhagen et al. | |
| 5,160,325 A | 11/1992 | Nichols et al. | |
| 5,167,623 A | 12/1992 | Cianci et al. | |
| 5,169,393 A | 12/1992 | Moorehead et al. | |
| 5,201,722 A | 4/1993 | Moorehead et al. | |
| 5,205,834 A | 4/1993 | Moorehead et al. | |
| 5,207,648 A | 5/1993 | Gross | |
| 5,292,305 A | 3/1994 | Boudewijn et al. | 604/43 |
| 5,318,588 A | 6/1994 | Horzewski et al. | 606/198 |
| 5,350,358 A | 9/1994 | Martin | |
| 5,380,276 A | 1/1995 | Miller et al. | 604/28 |
| 5,380,301 A | 1/1995 | Pritchard et al. | 604/533 |
| 5,405,339 A | 4/1995 | Kohnen et al. | |
| 5,409,455 A | 4/1995 | Belden | |
| 5,478,331 A | 12/1995 | Heflin et al. | |
| 5,556,386 A | 9/1996 | Todd | |
| 5,569,197 A | 10/1996 | Helmus et al. | 604/102.02 |
| 5,683,640 A | 11/1997 | Miller et al. | |
| 5,707,356 A | 1/1998 | Paul | |
| 5,713,849 A * | 2/1998 | Bosma et al. | 604/28 |
| 5,718,678 A | 2/1998 | Fleming, III | |
| 5,752,522 A | 5/1998 | Murphy | |
| 5,776,117 A | 7/1998 | Haselhorst et al. | |
| 5,797,869 A | 8/1998 | Martin et al. | |
| 5,830,196 A | 11/1998 | Hicks | 604/523 |
| 5,843,044 A | 12/1998 | Moorehead | |
| 5,902,282 A | 5/1999 | Balbierz | 604/264 |
| 5,961,485 A | 10/1999 | Martin | |
| 5,976,103 A | 11/1999 | Martin | |
| 5,984,902 A | 11/1999 | Moorehead | |
| 5,989,206 A | 11/1999 | Prosl et al. | 604/5.01 |
| 6,033,393 A | 3/2000 | Balbierz et al. | |
| 6,190,349 B1 | 2/2001 | Ash et al. | |
| 6,190,354 B1 | 2/2001 | Sell et al. | |
| 6,290,265 B1 | 9/2001 | Warburton-Pitt et al. | |
| 6,503,244 B2 | 1/2003 | Hayman | |
| 6,520,977 B2 | 2/2003 | Piraka | |
| 6,575,959 B1 | 6/2003 | Sarge et al. | 604/533 |
| 6,592,544 B1 * | 7/2003 | Mooney et al. | 604/43 |
| 6,595,966 B2 | 7/2003 | Davey et al. | 604/264 |
| 6,620,118 B1 | 9/2003 | Prosl et al. | 604/5.01 |
| 6,638,242 B2 | 10/2003 | Wilson et al. | |
| 6,689,096 B1 * | 2/2004 | Loubens et al. | 604/96.01 |
| 6,966,893 B2 | 11/2005 | Holtby et al. | |
| 7,025,716 B1 | 4/2006 | Meloul et al. | |
| 7,252,652 B2 | 8/2007 | Moorehead et al. | |
| 7,931,619 B2 | 4/2011 | Diamond et al. | |
| 2002/0062119 A1 | 5/2002 | Zadno-Azizi | |
| 2002/0099326 A1 | 7/2002 | Wilson et al. | |
| 2003/0088213 A1 | 5/2003 | Schweikert et al. | |
| 2003/0199853 A1 | 10/2003 | Olsen et al. | |
| 2004/0054348 A1 | 3/2004 | Hogendijk | |
| 2004/0243103 A1 | 12/2004 | King et al. | |
| 2005/0049555 A1 * | 3/2005 | Moorehead et al. | 604/122 |
| 2006/0089604 A1 * | 4/2006 | Guerrero | 604/247 |
| 2006/0149189 A1 | 7/2006 | Diamond et al. | |
| 2006/0276773 A1 | 12/2006 | Wilson et al. | |
| 2007/0093764 A1 | 4/2007 | Guerrero | |
| 2007/0129692 A1 | 6/2007 | Enomoto et al. | |
| 2007/0161940 A1 | 7/2007 | Blanchard et al. | |
| 2007/0173777 A1 | 7/2007 | Murphy | |
| 2007/0173786 A1 | 7/2007 | Recinella et al. | |

OTHER PUBLICATIONS

Steven G. Miles, MD et al., "Safe Use of an Intravenous Power Injector for CT: Experience and Protocol." Radiology (Jul. 1990) vol. 176, pp. 69-70.

Michael P. Federle, MD et al., "Frequency and Effects of Extravasation of Ionic and Nonionic CT Contrast Media During Rapid Bolus Injection." Radiology (Mar. 1998) vol. 206 No. 3, pp. 637-640.

Barbara Lowery, R.N. et al., "Modified Umbilical Artery Catheter for Power-Injection Aortography." Radiology (Dec. 1972) vol. 105, pp. 711-712.

Ari I. Salis, MD et al., "Maximal Flow Rates Possible During Power Injection Through Currently Available PICC's: an InVitro Study." J. Vaso. Interv. Radiology (Mar. 2004) vol. 15 No. 3, pp. 275-281.

Jill E. Jacobs, MD et al., "Contrast Media Reactions and Extravasation: Relationship to Intravenous Injection Rates." Radiology (Nov. 1998), vol. 209 No. 2, pp. 411-416.

Lynne Ruess, MD et al., "In-Line Pressures Generated in Small-Bore Central Venous Catheters During Power Injection of CT Contrast Media." Radiology (1997), vol. 203 No. 3, pp. 625-629.

Douglas Coyle, MD et al., "Power Injection of Contrast Media via Peripherally Inserted Central Catheters for CT." J. Vasc Interv Radiology (Aug. 2004), vol. 15 No. 8, pp. 809-814.

Daniel B. Brown, MD et al., "Power Injection of Microcatheters: An in Vitro Comparison." J. Vasc Interv Radiology (Jan. 2005), vol. 16 No. 1, pp. 101-106.

Pina C. Sanelli et al., "Safety and Feasibility of Using a Central Venous Catheter for Rapid Contrast Injection Rates." AJR: 183 (Dec. 2004), pp. 1829-1834.

Brian R. Herts, MD et al., "Power Injection of Intravenous Contrast Material Through Central Venous Catheters for CT: In Vitro Evaluation." Radiology (Sep. 1996), vol. 200 No. 3, pp. 731-735.

Eric E. Wiliamson et al., "Assessing the Adequacy of Peripherally Inserted Central Catheters for Power Injection of Intravenous Contrast Agents for CT." Journal of computer Assisted Tomography (2001), vol. 25 No. 6, pp. 932-937.

S. Mitchell Rivits, MD et al., "Power Injection of Peripherally Inserted Central Catheters." Journal of Vascular and Interventional Radiology (Sep.-Oct. 1997), vol. 8 No. 5, pp. 857-863.

EP 1628700 filed May 25, 2005 Office Action dated Jun. 11, 2007.
EP 1628700 filed May 25, 2005 Office Action dated Nov. 25, 2010.
PCT/US2004/016595 filed May 25, 2004 International Preliminary Report on Patentability dated Oct. 21, 2005.
PCT/US2004/016595 filed May 25, 2004 Search Report dated Oct. 1, 2004.
PCT/US2004/016595 filed May 25, 2004 Written Opinion dated Oct. 1, 2004.
U.S. Appl. No. 10/853,076, filed May 25, 2004 Final Office Action dated Jul. 24, 2009.
U.S. Appl. No. 10/853,076, filed May 25, 2004 Final Office Action dated Oct. 16, 2007.
U.S. Appl. No. 10/853,076, filed May 25, 2004 Non-Final Office Action dated Jun. 25, 2007.
U.S. Appl. No. 10/853,076, filed May 25, 2004 Non-Final Office Action dated Mar. 12, 2008.
U.S. Appl. No. 11/029,299, filed Jan. 4, 2005 Final Office Action dated Apr. 16, 2010.

(56) References Cited

OTHER PUBLICATIONS

U.S. Appl. No. 11/029,299, filed Jan. 4, 2005 Final Office Action dated Oct. 1, 2008.
U.S. Appl. No. 11/029,299, filed Jan. 4, 2005 Non-Final Office Action dated Dec. 7, 2009.
U.S. Appl. No. 11/029,299, filed Jan. 4, 2005 Non-Final Office Action dated Jun. 19, 2009.
U.S. Appl. No. 11/029,299, filed Jan. 4, 2005 Non-Final Office Action dated Mar. 19, 2008.
U.S. Appl. No. 11/029,299, filed Jan. 4, 2005 Notice of Allowance dated Dec. 23, 2010.

* cited by examiner

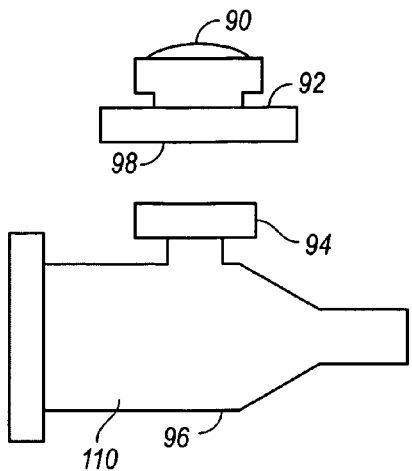 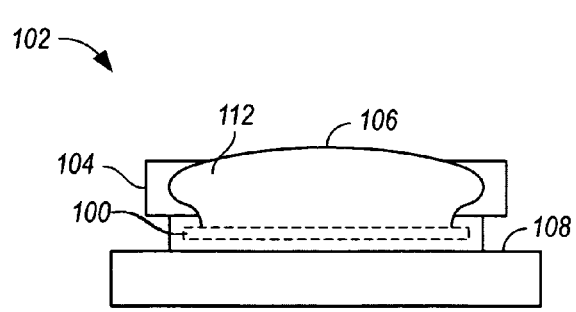
FIG. 5A                    FIG. 5B
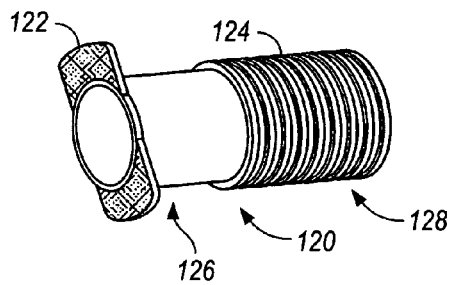
FIG. 6A
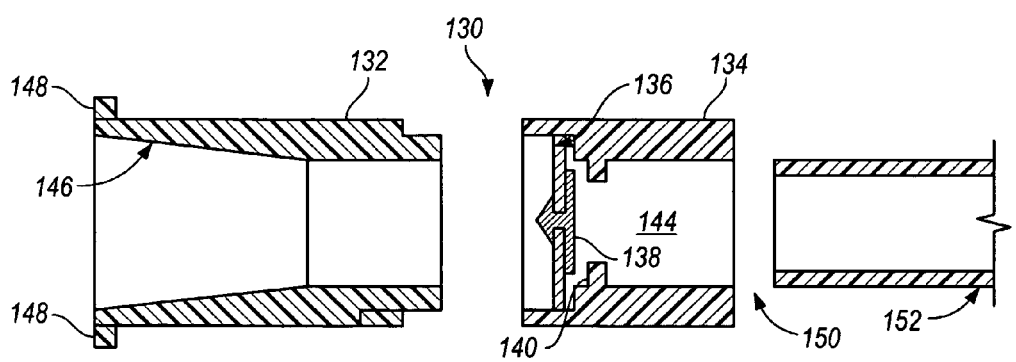
FIG. 6B

POWER INJECTION CATHETERS AND METHOD OF INJECTING

CROSS-REFERENCE TO RELATED APPLICATIONS

This application is a continuation-in-part of U.S. patent application Ser. No. 11/029,299, filed Jan. 4, 2005, now U.S. Pat. No. 7,931,619, the disclosure of which is incorporated, in its entirety, by this reference.

BACKGROUND

It has been observed that during injection of a contrast media at high flow rates into a small-sized lumen, the sudden increase in pressure inside the lumen may lead to failure of the catheter wall. In addition, catheters that are implanted in a patient's body for a period of time may have thrombus build-up within the lumen of the catheter. These thromboses may occlude the catheter and cause overpressurization when the catheter is flushed. To prevent the sudden pressure spikes, a pressure buffering component may be provided to modulate the pressure inside the catheter lumen. Various other medical applications that require high throughput fluid injection through a catheter may also benefit from having a pressure modulating device integrated within the catheter to prevent overpressurizing and/or to provide an indicator to the operator that the catheter is being overloaded.

Examples of various overpressure protection devices are disclosed in U.S. Pat. No. 3,543,759, titled "CATHETER WITH SAFETY INDICATOR" issued to McWhorter, dated Dec. 1, 1970; U.S. Pat. No. 4,000,741, titled "SYRINGE ASSEMBLY" issued to Binard et al., dated Jan. 4, 1977; U.S. Pat. No. 4,240,430, titled "SYRINGE ASSEMBLY" issued to Binard et al., dated Dec. 23, 1980; U.S. Pat. No. 4,403,988, titled "SYRINGE ASSEMBLY" issued to Binard et al., dated Sep. 13, 1983; U.S. Pat. No. 4,671,786, titled "OVERPRESSURE SAFETY VALVE" issued to Krug, dated Jun. 9, 1987; U.S. Pat. No. 6,033,393, titled "METHOD AND APPARATUS FOR OVERPRESSURE PROTECTION OF A CATHETER" issued to Balbierz et al., dated Mar. 7, 2000; U.S. Pat. No. 6,520,977 B2, titled "UTERINE BALLOON APPARATUS AND METHOD" issued to Piraka, dated Feb. 18, 2003; each of which is incorporated herein by reference in its entirety.

Many of the devices disclosed above are design for low flow applications. Furthermore, in a pressure protection device that is based on a compliant balloon, the balloon will typically enlarge gradually in response to pressure, and therefore does not provide a clear indication to the operator when a critical pressure threshold has been breached. Thus, in applications where high pressure injections are required, the operators may have difficulty determining whether overpressurization has occurred by observing the condition of a partially inflated balloon alone. In addition, many of these designs may fail at high pressure, such as 300 psi or above. The compliant nature of the pressure protection mechanisms in these devices may also prevent high pressure from being maintained within the catheter, since many of the compliant balloons will start to expand at a relatively low pressure. These designs tend to have a low pressure threshold, and, as a result, the overall fluid throughput is also relatively low. In addition, many of the disclosed devices have flow paths with high flow resistance.

For power injection applications where a high fluid infusion rate is necessary, it may be desirable to have a pressure buffering device that allows one to maintain high pressure, such as 300 psi or above, within the lumen of the catheter, but at the same time is capable of modulating sudden pressure peaks. Sudden pressure spikes due to initial introduction of fluid pressure, unanticipated obstruction within the catheter, or operator error, may temporarily force the pressure inside the catheter to exceed the breaking threshold (i.e., burst value) of the catheter. However, for high flow rate injection a relatively high pressure needs to be maintained within the catheter to maintain the high throughput. Thus, a device that can prevent pressure spikes and overpressurization, but at the same time allows the system to maintain a relatively high pressure within the catheter to support high flow rate application may be desirable.

In addition, it may be desirable to have a catheter that can be configured with a low resistance flow path to maximize flow rate for power injection applications. A catheter that can be configured to minimize flow resistance and support high fluid flow rate may be particularly useful for power injection applications.

BRIEF SUMMARY

Described herein are catheters for infusing fluids into a patient's body. Some variations of the catheter are configured for high flow rate applications. These catheters, which are configured for infusing large amounts of fluids in a short period of time, are termed "power injection catheters." The catheters may be configured to support high pressure inside its lumen to sustain high pressure generated by rapid infusion. In addition, a pressure relief mechanism may be provided on the catheter to prevent overpressurization.

One aspect of the instant disclosure relates to a catheter comprising an elongated catheter body including a proximal end and a distal end, the body defining one lumen. More particularly, the catheter may comprise a plurality of extension tubes, each of the plurality of extension tubes comprising a lumen in fluid communication with the one lumen of the catheter body. Further, a first of the plurality of extension tubes may be configured for performing power injection and a second of the plurality of extension tubes may include a proximal valve.

Another aspect of the instant disclosure relates to a catheter comprising an elongated catheter body including a proximal end and a distal end, the body defining a plurality of lumens. More particularly, the catheter may comprise a plurality of extension tubes, each of the plurality of extension tubes comprising a lumen in fluid communication with one lumen of the plurality of lumens of the catheter body, respectively. Further, at least one of the plurality of extension tubes may be configured for performing power injection and at least one of the plurality of extension tubes may include a proximal valve.

Also, a further aspect of the instant disclosure relates to a method of injecting a fluid into a patient's body. Specifically, a catheter may be inserted into a circulatory system of a patient. In further detail, the catheter may include at least one lumen and at least one extension tube comprising a proximal valve, the at least one extension tube capable of fluid communication with the at least one lumen of the catheter. Also, the proximal valve may be structured to inhibit fluid flow for pressures developed within the at least one lumen of the catheter below a selected aspiration pressure. A pressure exceeding the selected aspiration pressure may be developed within the at least one lumen of the catheter by injecting a fluid into the at least one lumen of the catheter. Additionally, fluid flow through the at least one extension tube comprising the proximal valve may be prevented.

Features from any of the above mentioned embodiments may be used in combination with one another in accordance with the instant disclosure. In addition, these and other embodiments, features and advantages of the instant disclosure will become more apparent to those skilled in the art when taken with reference to the following more detailed description in conjunction with the accompanying drawings that are first briefly described.

BRIEF DESCRIPTION OF THE DRAWINGS

FIG. 5A illustrates another variation of a pressure relief device with a replaceable pressure relief valve for covering the side port.

FIG. 5B shows one variation of a replaceable cap for the pressure relief valve of FIG. 5A. In this variation, the replaceable pressure relief valve has a built-in balloon and a burst disk for relieving overpressure.

FIG. 6A illustrates another design variation comprised of an inline valve. The inline valve prevents overpressuring of the catheter lumen by blocking further fluid input when there is a sudden surge in pressure inside the catheter.

FIG. 6B shows a cross-sectional view of the pressure check valve of FIG. 6A.

DETAILED DESCRIPTION

The following detailed description should be read with reference to the drawings, in which like elements in different drawings may be identically numbered. The drawings, which are not necessarily to scale, depict selected preferred embodiments and are not intended to limit the scope of the present invention. The detailed description illustrates by way of example, not by way of limitation, the principles of the present invention. This description will clearly enable one skilled in the art to make and use the invention, and describes several embodiments, adaptations, alternatives and uses of the invention, including what is presently believed to be the best mode of carrying out the invention.

Before describing aspects of the present invention, it is to be understood that, unless otherwise indicated, this invention need not be limited to applications in humans. As one of ordinary skill in the art would appreciate, variations of the invention may be applied to other mammals as well. Moreover, it should be understood that embodiments of the present invention may be applied in combination with various catheters, drug pumps, and infusion devices.

A Peripherally Inserted Central Catheter (PICC) is used herein as an example application of the power injection catheter to illustrate the various aspects of the invention disclosed herein. One of ordinary skill in the art having the benefit of this disclosure would appreciate that the power injection catheter disclosed herein may be applicable for infusion of fluids into the circulatory system in various medical applications. It is also contemplated that the pressure relief device described herein may be implemented with various fluid infusion lines and catheters, including, but not limited to, hemodialysis catheters, central line catheters and contrast dye injection catheters.

It must also be noted that, as used in this specification and the appended claims, the singular forms "a," "an" and "the" include plural referents unless the context clearly dictates otherwise. Thus, for example, the term "a lumen" is intended to mean a single lumen or a combination of lumens, "a fluid" is intended to mean one or more fluids, or a mixture thereof.

Figure 1:
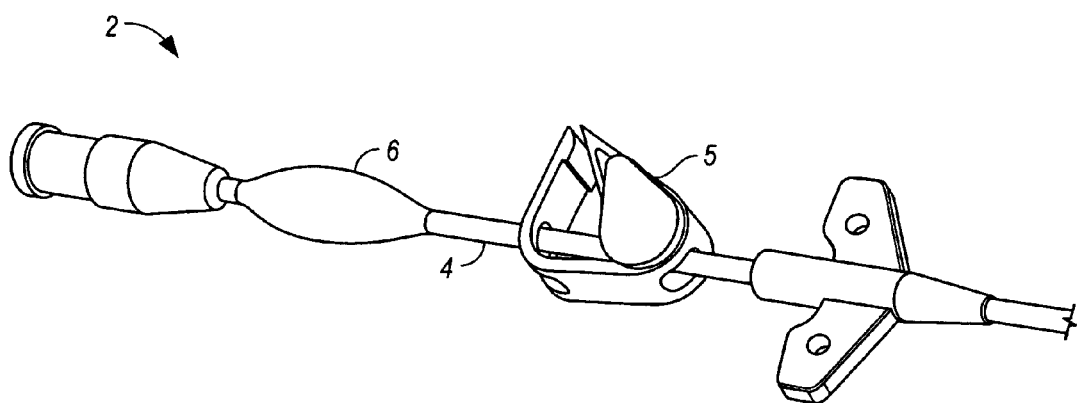
FIG. 1 illustrates one variation of a power injection catheter with a pressure relief balloon integrated into the proximal shaft of the catheter.

In one aspect of the present invention, a catheter 2 comprises an elongated tubing with a pressure relief balloon 6 integrated within the body of the catheter. In one variation, the balloon 6 is integrated along the extension leg 4 of the catheter 2, as shown, for example, in FIG. 1. An optional clip 5 may be provided on the extension leg 4 to allow the user to temporarily seal the lumen of the extension leg. In another variation, the balloon may be connected to the catheter through a branch connection. The interior of the balloon is in fluid communication with the lumen of the catheter. The balloon may be comprised of a compliant, semi-compliant, or non-compliant material. In one particular variation, a non-compliant pressure relief balloon is implemented. A non-compliant balloon may provide buffering to a sudden pressure increase, but at the same time allow the operator to maintain high pressure to push the fluids through the catheter at a high rate (e.g., about 3 cc/sec or higher). For example, a typical compliant balloon may inflate at a lower pressure, such as about 100 psi, and continue to expand at pressure slightly above this value until the balloon bursts. Thus, the balloon would prevent the operator to continue to increase the pressure inside the lumen of the catheter. In a catheter with a small inner lumen, if the infusion pressure is limited, then the catheter would not be able to achieve high flow rate.

However, with a semi-compliant or non-compliant balloon, one may select materials to construct a balloon with a high burst value. For general PICC power injection applications, in one variation the balloon is configured with a burst value above about 100 psi; in another variation, the balloon is configured with a burst value above about 130 psi; in yet another variation, the balloon is configured with a burst value of at least about 200 psi. In a design with a non-compliant balloon with a high burst value, the operator is able to maintain high pressure (e.g., about 130 psi or above; in selective designs about 300 psi or above can be supported) within the lumen of the catheter to push the fluids through the catheter lumen at a high flow rate (e.g., about 4 cc/sec or above; in selective designs about 5 cc/sec or above can be supported). This design may provide the benefit of including a pressure buffering device (i.e., the pressure relief balloon) while at the same time allowing the operator to use the catheter for power injection applications (e.g., injection of contrast media at high flow rates, etc.), which require high pressures to maintain the high flow rate. As one of ordinary skill would appreciate, to achieve high flow rates one can increase the catheter lumen diameter and/or increase the pressure applied to infuse the fluid. Since the diameter of the catheter is limited by the dimension of the vessel that it's designed for, in many applications high pressures are required to maintain the high flow rate in catheters with a relatively small lumen size.

The pressure relief balloon of the present invention allows the device to buffer against sudden pressure increases, which may cause pressure spikes that exceed the catheter's burst value. The catheter body may be rated with a high burst value, but sudden pressure increases due to operator error or other factors may cause a temporary increase in pressure that exceeds the pressure threshold supported by the catheter. Without a pressure buffering medium, the catheter will likely burst. With a pressure relieving balloon, however, the pressure spike may be modulated and destruction of the catheter may be avoided.

Furthermore, one may configure the pressure relief balloon such that the balloon has a burst value that is below the burst value of the catheter. For example, the catheter body may be rated with a burst value of about 450 psi and the pressure relief balloon may be configured with a burst value of about 400 psi. In this design, when overpressure is so high (above about 400 psi), such that the balloon is unable to modulate the increased pressure, the balloon positioned at the proximal portion of the catheter will fail first and prevent damage to the catheter. Since the balloon is located at the proximal portion at the exterior of the body, it can be easily replaced or repaired without the need to surgically remove and replace the complete catheter. In another variation, one may configure the balloon such that the balloon expands minimally with moderate pressure (e.g., under about 300 psi) and expands at a much higher rate at a higher pressure (e.g., pressure above about 300 psi). In another variation, the balloon may further be configured to expand at a pressure close to the burst value of the catheter. For example, the burst value of the catheter may be about 400 psi, while the balloon expands at a higher rate at pressure above about 350 psi. In such a configuration, the expansion of the balloon indicates to the operator that the inner lumen pressure has exceeded a certain pressure threshold and the integrity of the catheter is at risk.

In the above catheter configurations, the balloon may be replaced with a diaphragm integrated within a housing including a fluid conduit. For example, a housing with a diaphragm may take the place of the balloon 6 on the device shown in FIG. 1. The fluid conduit within the housing allows the fluid to flow through, and the diaphragm serves as the pressure buffering mechanism. The diaphragm may be comprised of a compliant or semi-compliant material. In one particular variation, the diaphragm comprises a non-compliant polymeric material.

As discussed above, the balloon or diaphragm may be integrated into the external (proximal) portion of the catheter. The balloon or diaphragm serves to relieve pressure build-up and at the same time serve as a visual indicator to the operator that the catheter may be occluded and/or overpressurized. The balloon or diaphragm may also be added as an extension tube and becomes an integral part of the extension leg of the catheter. The balloon or diaphragm may be comprised of various polymeric materials or mixture thereof. For example, the balloon or diaphragm may be made of a single or double layer nylon material or of a composite material. The balloon or diaphragm may also be added to the catheter's proximal end connector and become an integral part of the connector. One of ordinary skill in the art having the benefit of the disclosure herein would appreciate that various balloon and tubing technologies that are well known in the art may also be implemented in the designs disclosed herein.

Figure 2A:
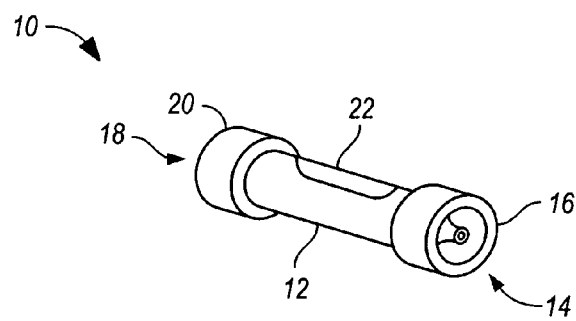
FIG. 2A illustrates a catheter inter-connector with a built-in diaphragm for modulating pressure inside the lumen of the inter-connector.
Figure 2B:
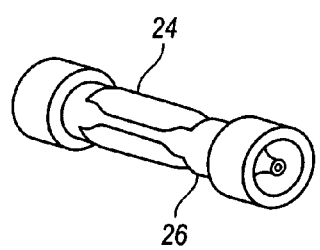
FIG. 2B illustrates a catheter inter-connector with a built-in balloon for modulating the pressure of fluid flow going through the inter-connector.

In another variation, the pressure relief device comprises an inter-connector with a built-in diaphragm. For example, the device 10 may comprise an inter-connecting tubing 12 with a male Luer Lock interface 14 at the distal end 16 of the tubing and a female Luer Lock interface 18 at the proximal end 20 of the tubing, as shown in FIG. 2A. A diaphragm 22 is provided at the mid-section of the tubing for relieving pressure build-up in the lumen of the inter-connector 12. FIG. 2B illustrates another variation of a pressure relief inter-connector where a balloon 24 is integrated into the body of the inter-connector 26. The pressure relief inter-connector may be connected to the proximal end of a catheter to provide pressure modulation to the lumen of the catheter. A fluid source may then be connected to the proximal end of the inter-connector to supply fluids into the lumen of the catheter through the inter-connector. In another variation, the pressure relieving inter-connector may be placed between two inter-connecting tubings to provide pressure modulation within the lumens of the tubing.

The diaphragm or balloon within the inter-connector may be comprised of compliant, semi-compliant, or non-compliant polymeric material. The various diaphragms and balloons described above with specific burst value or expansion characteristics may also be implemented within the inter-connector. For example, the balloon in the inter-connector may comprise a non-compliant balloon with a burst value of at least about 300 psi. In another variation, an inter-connector including a balloon or diaphragm with a lower burst value than the catheter is connected to the proximal end of the catheter to provide a fail-safe mechanism for the catheter. For example, an inter-connector with a diaphragm having a burst value of about 300 psi is connected to the proximal end of a catheter having a burst value of about 330 psi. In this variation, the inter-connector may prevent failure of the catheter due to overpressurizing since the diaphragm within the inter-connector would fail first. Since the inter-connector is removable, once it fails it can be quickly replaced and allow the medical procedure to proceed without much interruption.

Figure 2C:
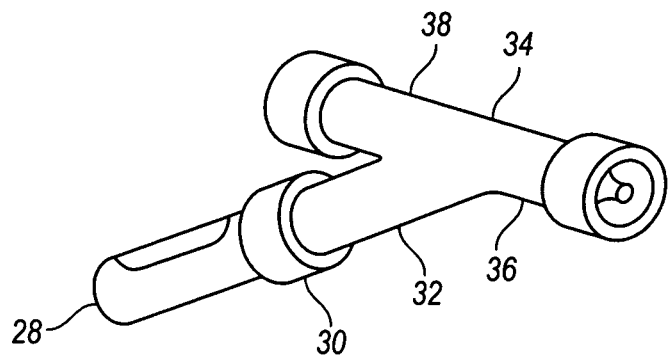
FIG. 2C illustrates another variation of a pressure relief device design where the pressure relief mechanism is provided on a side branch of a bifurcating connector.

In another variation, the inter-connectors shown in FIGS. 2A and 2B are modified with one sealed end 28 and one connection end 30. The connection end 30 of the device may be connected to a first bifurcation arm 32 of a "Y" connector 34, as shown in FIG. 2C. The primary arm 36 of the "Y" connector 34 may be connected to the proximal end of a catheter and the second bifurcating arm 38 of the "Y" connector 34 may be connected to a syringe or a fluid source. Since the pressure relieving unit is in fluid communication with the lumen of the catheter through the "Y" connector 34, the pressure relieving unit can modulate fluid pressure inside the catheter. In one variation, the pressure relieving unit may be permanently connected to the "Y" connector. In another variation, a removable pressure relieving unit is connected to the "Y" connector through an inter-connecting mechanism, such as a Luer Lock interface.

Figure 3A:
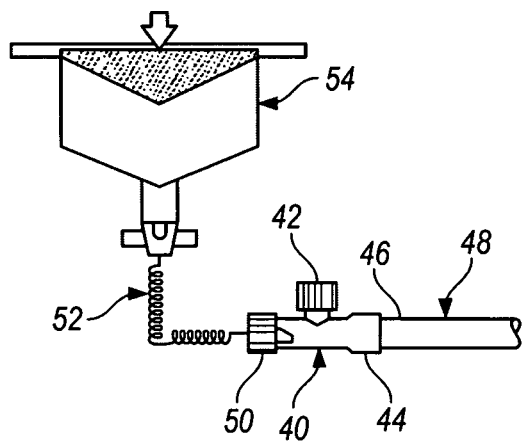
FIG. 3A illustrates a pressure relief device including one end connected to a fluid injection device and the other end connected to the proximal end of a catheter. In this variation, the pressure relief device has a pressure relief port for releasing or absorbing overpressure that occurs inside the lumen of the device.
Figure 3B:
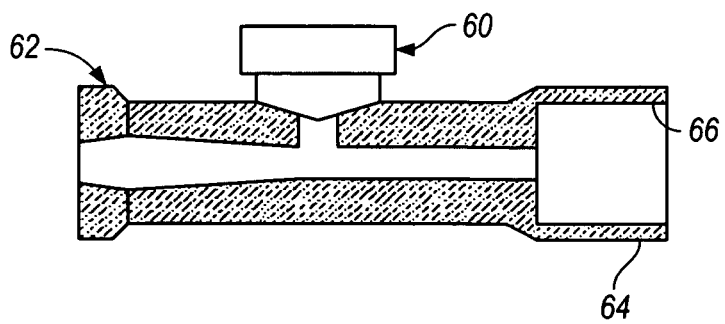
FIG. 3B shows a semi-transparent view of the pressure relief device of FIG. 3A.

In yet another variation, the inter-connecting pressure relief device comprises a side port with a pressure relieving mechanism. For example, the device may be a "T" connector with the distal port configured for connection to a catheter, the proximal port configured for connection to a syringe or fluid infusion source, and a side port configured with a pressure relief mechanism, such as a pressure relief valve, a balloon, a burst disk, or a diaphragm. In one example shown in FIG. 3A, the connector 40 has a built-in pressure relief valve in the side port 42. The distal end 44 of the connector 40 connects to the proximal end 46 of a power PICC catheter 48 through a Luer Lock interface. The proximal end 50 of the "T" connector 40 also has a Luer Lock connection for connecting to a tubing 52 to receive fluid from a power injection fluid source 54. In one variation, the power injection device 54 is configured with a capability of delivering a maximum pressure of about 300 psi. FIG. 3B shows a cross-sectional view of another variation of a pressure relief device. The side port 60 houses the pressure relief valve. The proximal end 62 has a female Luer Lock attachment for connection to a syringe or other tubing such as a coiled extension set. The distal end 64 has a C-Bore 66 feature to accept a power PICC tubing. In another variation, the distal end 64 may be configured with a male Luer Lock interface for connection to a catheter including a female Luer Lock interface at its proximal end.

Figure 4:
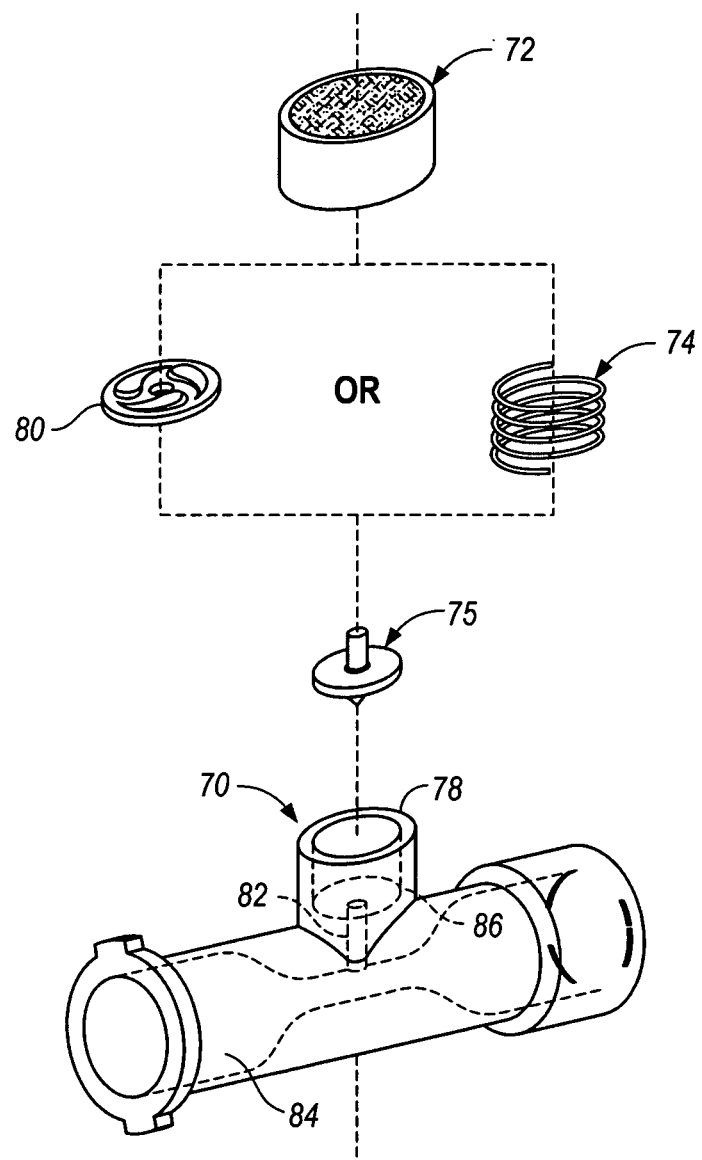
FIG. 4 illustrates one variation of a pressure relief device with a pressure relief valve incorporated in the side port of the device. The device is shown with the pressure relief valve in a disassembled state.

In one particular design, a pressure relief valve 70 comprises a spring-loaded plunger as shown in FIG. 4. A diffuser cap 72 and/or Luer Lock attachment is provided to secure a spring 74, 80 and plunger elements 76 within the side port 78. The diffuser cap 72 allows the effluent from overpressure to escape. The diffuser cap 72 may be mechanically jointed to the side port 78. A coil 74 or etched flat spring 80 is provided to maintain pressure on the plunger 76. A channel 82 within the device provides fluid communication between the lumen 84 of the inter-connector and the side port 78. Within the base of the side port, a valve seat 86 is provided to receive the plunger 76. The size of the valve seat 86 establishes the area of the valve mechanism exposed to pressure. The plunger 76 creates a seal when closed by the spring force. When the fluid flowing through the inner channel 82 into the valve seat 86 in the side port 78 builds up a pressure exceeding the force from the spring, the plunger is displaced.

The pressure from the power injection device transfers through the fluid channel and acts on the exposed area of the pressure relief valve. The exposed area multiplied by the effective pressure yields a resultant force. The resultant force of the fluid acting on the plunger/seal in the pressure relief valve is opposed by the loaded spring, which keeps the valve in the normally closed position. The magnitude of the spring force '$F_s$' is a function of the spring constant 'k' and the displacement distance 'x' (i.e., $F_s=k*x$). The magnitude of the resultant force from the fluid '$F_f$' applied on the plunger from the fluid pressure is proportional to the fluid pressure 'P' and the exposed area 'A' of the plunger (i.e., $F_f=P*A$). The interaction between the two forces, '$F_s$' and '$F_f$', determines the displacement of the plunger and the release of fluid from the pressure relief valve. Thus, by varying the size of the valve seat, the size of the plunger/valve, and the tension of the spring, one can configure the pressure relief valve to release pressure at a specific pressure threshold level.

In another variation of a pressure relief inter-connector, the device is configured with a replaceable pressure relief mechanism (e.g., pressure relief valve, diaphragm, balloon, etc.). The pressure relief mechanism 90 may be integrated into a cap 92 that can be mechanically connected to a side port 94 of an inter-connector 96, as shown in FIG. 5A. For example, the base 98 of the cap may have female thread matching the male thread on the side port 94 of the inter-connector, such that the cap can be easily attached to, or removed from, the inter-connector 96. Since the cap 92 is removable and replaceable, once the pressure relief mechanism 90 fails, the operator may replace it with another cap that is functional. In another variation, during the medical procedure the operator may wish to replace an existing cap with a different one that has a higher or lower pressure rating or performance characteristic in comparison with the existing one.

In one variation, the cap has an integrated balloon for pressure buffering. The balloon may be comprised of a compliant, semi-compliant or non-compliant material. For some applications, it may be desirable to implement a balloon comprising a non-compliant material. One may also select a balloon of specific burst value for implementation on the cap. For example, for power injection application where high flow (e.g., capable of delivering about 4 cc/sec or more) is required, it may be desirable to select a cap with a balloon that has a burst value of at least about 300 psi. In another variation, one may implement a cap with a burst value that is below the burst value of the catheter body, such that the balloon in the cap bursts before the catheter is overpressurized. This allows the operator to prevent accidental overpressurizing of the catheter. In the event that the balloon in the cap bursts, the operator can replace the damaged cap and proceed with the medical procedure. In another variation, a diaphragm is implemented in the replaceable cap in place of the balloon. Various material selection considerations (e.g., compliance, burst value, expansion value, etc.) that are implemented for balloon selection are also applicable for the selection of the polymeric materials for the implementation of the diaphragm.

In another design variation, a burst disk is provided between a pressure relief device and the lumen of the catheter, such that the pressure relief device is only activated when the pressure inside the lumen of the catheter exceeds the threshold of the burst disk and compromises the integrity of the burst disk (e.g., causing the burst disk to rupture), allowing the fluid inside the catheter to flow toward the pressure relief device. For example, one may select a burst disk with a burst value that is below the burst value of the catheter body, such that the burst disk will rupture and activate the pressure relief device (e.g., balloon, diaphragm, pressure relief valve, etc.) before the catheter is overpressurized.

In one variation, the burst disk 100 is integrated within a replaceable cap 102 as shown in FIG. 5B. The cap with the burst disk 100 may be utilized on an inter-connector 96 shown in FIG. 5A. Referring to FIG. 5B, the cap 102 comprises a housing 104 for securing a containment balloon 106 and allows for deployment of the balloon. The containment balloon 106 may comprise an elastomeric or non-elastic folded/wrapped material similar to the configuration of an airbag or angioplasty balloon. In one variation, the balloon 106 is configured with a capacity of at least about 3 cc. The containment balloon 106 may also comprise a non-compliant material. A burst disk 100 is provided on the base 108 of the housing. When the cap 102 is secured onto the inter-connector 96, the burst disk 100 provides the interface between the lumen 110 of the inter-connector 96 and the cavity 112 between the balloon 106 and the burst disk 100. The pressure threshold or burst value of the burst disk 100 may be varied by changing the materials and thickness of the burst disk. Higher strength materials and thickness may be used to achieve pressure compatible with power injection. In a particular design, the burst disk is configured to rupture before the catheter body is overpressurized and is caused to fail. For example, the burst disk may be comprised of the same polymeric material as the catheter with some modification to the material to weaken its strength or to decrease its thickness, such that the maximum pressure the burst disk can sustain is less than the maximum sustainable pressure of the catheter wall.

In one particular design, the catheter comprises a 3-French silicone catheter of A durometer (about 0.007 to about 0.009 inch wall thickness). Burst disks of various configurations may be applicable for integration with the 3-French catheter to prevent overpressurization. In one variation, the burst disk comprises silicone of approximately 50 A durometer. In another variation, the burst disk comprises the same silicone material used to fabricate the catheter, but the disk is configured with a thickness of less than about 0.007 inches. In yet another variation, the burst disk is implemented on the catheter itself by localized weakening of catheter body using a scribe line, etching, localized thinning, etc., such that the weakened region will burst before the catheter is overpressurized. Furthermore, grooves or indentations may be etched into the catheter body as part of the localized weakening process. In one design variation, the weakened region is located at the proximal portion of the catheter.

In another design variation, a 6-French polyurethane catheter of about 78 A durometer (about 0.013 to about 0.017 inch wall thickness) is implemented with a burst disk. In one variation, polyurethane of approximately 70 A durometer is used to configure the burst disk. In another variation, the burst disk comprises silicone of approximately 70 to 80 A durometer (silicone typically has a lower burst and tear strength than polyurethane). In another variation, the burst disk comprises a sheet of material having a thickness of less than about 0.013 inches. In yet another variation, localized weakening of the catheter wall is used to implement a burst disk on a selective location directly on the catheter wall. As one of ordinary skill in the art having benefit of the disclosure herein will appreciate, the above variations may also be implemented on a multi-lumen catheter to provide a burst disk or other pressure relief mechanism for the catheter. In one variation, all the lumens in the multi-lumen catheter share the same burst disk as the pressure relief mechanism. In another variation, each lumen within the catheter is equipped with its own burst disk or pressure relief mechanism.

In another design variation, a diaphragm is used in placed of the containment balloon. For example, the housing in the cap may secure a diaphragm comprised of a compliant material while a burst disk is provided at the base of the housing, such that the diaphragm only expands if the pressure inside the lumen of the catheter overcomes the burst disk and forces the burst disk to rupture. In another variation, the burst disk may be implemented with a pressure relief valve. In yet another design variation, the burst disk is implemented as the sole pressure relief mechanism without the additional balloon, diaphragm or pressure relief valve. In such a design, the fluid inside the catheter may exit the delivery system through the burst disk once the burst disk is compromised (e.g., ruptures).

As one of ordinary skill in the art having the benefit of the disclosure herein would appreciate, the implementation of the burst disk is not limited to the removable cap configuration. The burst disk may be integrated in various inter-connectors or directly on the body of the catheter, either along with other pressure relief mechanisms (e.g., balloon, diaphragm, pressure relief valve, etc.), or independently without the other pressure relief mechanisms. Furthermore, the burst disk may comprise various configurations, including, but not limited to, a disk shape. The burst disk may be comprised of compliant, semi-compliant, or non-compliant materials. The burst disk may also be configured as a membrane, or other layer of materials integrated directly into the catheter or through an attachment interface. In one design variation, the burst disk is configured such that it will be compromised (burst) and allow fluids to pass through once the pressure being exerted on it exceeds a predefined threshold.

In another aspect of the present invention, an inline valve is integrated within a catheter or along the fluid path supplying fluids into the lumen of a catheter. The valve is configured such that when the pressure across the inline valve exceeds a predefined threshold, the inline valve is sealed and blocks further infusion of fluid through the valve; thus preventing the catheter, which is downstream from the valve, from overpressurizing. The inline valve may be integrated directly into the catheter or may be integrated within an inter-connector and then connected to the proximal end of a catheter. In one variation, the inline valve is positioned at the proximal portion of the catheter such that when the catheter is inserted inside the patient, the inline valve is outside the body. In this configuration, overpressurizing may be isolated to the portion of the catheter outside of the body and the portion of the catheter inside of the body is protected from overpressurizing. Furthermore, pressure relief mechanisms (e.g., balloon, diaphragm, pressure relief valve, etc.) may be provided in the fluid path upstream/proximal of the inline valve to prevent overpressurizing of the fluid supply line, which provides fluids to the catheter through the inline valve.

The inline valve for a catheter may be configured for attachment to the proximal end of a catheter or for insertion in between fluid supply lines. In one variation, the inline valve is integrated within an inter-connector 120 as shown in FIG. 6A. The proximal end 122 is configured for connection to a fluid supply source and the distal end 124 is configured for connection to a catheter, which is configured for insertion into a patient's body. Both the proximal 122 and the distal end 124 of the inline valve may be configured with tubing interface or connector (e.g., male/female Luer Lock or Luer Slip connections, etc.) for removable connection to catheters and/or other tubings. In the particular variation shown in FIG. 6A, the upper housing 126 is configured with a female Luer Lock interface for connection to tubings, coiled extension sets, syringes, or other fluid sources that have a male Luer Lock interface. The lower housing 128 is configured with a C-Bore in the inner lumen for solvent bond to a catheter. Alternatively, the lower housing 128 may also be configured with a removable connection interface such as a Luer Lock or Luer Slip. For example, the distal end of the lower housing may be configured with a male Luer Lock interface for receiving a female Luer Lock interface on the proximal end of a catheter. In another variation, both the proximal end and the distal end of the device are each permanently connected to a tubing.

Referring to FIG. 6B, the internal function of one variation of an inline valve 130 is illustrated in a cross-sectional view. The inline valve is housed within an inter-connector and comprises two connecting pieces 132, 134. An etched flat spring 136 is captured between the upper 132 and the lower 134 housing when the two housing pieces are connected to each other. The two-piece housing may be configured with solvent bond surfaces to achieve a sealed connection. In another variation, a locking interface such as matching threads may be provided on the corresponding part to secure the two housing pieces together. An elastomer seal 138 is suspended over the valve seat 140 by a flat spring 136, with fluids flowing through the flat spring 136 and around the elastomer seal 138. When the pressure difference between the inner lumen 142 of the upper housing and the inner lumen 144 of the lower housing is low, the spring 136 keeps the elastomer seal 138 away from the valve seat 140 and the fluid is allowed to flow through. When this pressure gradient overcomes the spring force, the elastomer seal 138 is forced down onto the valve seat 140 thereby arresting fluid flow through the inline valve. Once the pressure in the upper housing lumen 142 is decreased, such that the pressure across the valve is below the predefined threshold, the valve is opened to again permit fluid flow therethrough. Although in this variation an etched flat spring 136 is used to suspend the seal 138 and counteract the pressure from fluid flow, other spring materials or elastic materials may also be used in place of the etched flat spring. Furthermore, in this particular variation shown in FIG. 6B, the upper housing 132 is configured with a female Luer taper 146 in the proximal portion of the inner lumen 142 for receiving a male Luer. Luer ears 148 are provided at the proximal edge of the housing for mating with threads in a male Luer Lock interface. The distal portion 150 of the lower housing 134 is configured for receiving a catheter 152. The catheter 152 may be solvent bond to the lower housing 134.

In another variation, the inline valve is configured, such that the valve closes before the pressure inside the lumen of the catheter connected to the distal end of the inline valve exceeds its bursting pressure. For example, one may select a spring with a higher spring coefficient for a catheter having a high burst value, while using a spring with a lower spring coefficient for applications where a catheter with a lower burst value is being implemented. In another application, inter-connectors with embedded inline valves of varying sealing/closing pressure threshold may be provided, such that the operator may select the desired overpressure protection by connecting the appropriate inline valve to the proximal end of the catheter. For example, the catheter may have a burst pressure of about 400 psi, thus, one may design the inline valve to close before the pressure across the valve reaches about 300 psi to prevent the catheter from being overpressurized.

In another aspect of the invention, a multi-lumen catheter is configured for high flow infusion applications. A catheter having a plurality of lumens is designed, such that different fluids may be injected through the various lumens independently, or the operator may reconfigure the catheter, such that all the lumens are used simultaneously to deliver fluid from a single source at a high flow rate. For example, an elongated catheter body having a plurality of lumens running in parallel from the proximal end of the catheter to the distal end of the catheter may be prepared with a plurality of extension tubings connected to the proximal end of the catheter body for providing independent fluid paths to each of the lumens within the catheter body. A fluid inter-connector with multiple branching is attached to the proximal end of the first extension tubing. The fluid inter-connector has an input port and a plurality of output ports for connection to the proximal end of the plurality of extension tubings. The connection to the first tubing may be a permanent connection or it may be achieved through a Luer Lock type interlocking connection. Sealing caps may be implemented to close the unused output ports when the input port on the inter-connector is used for fluid delivery into the first tubing only. When the catheter is to be used for simultaneous injections of a single fluid through all the lumens, the sealing cap may be removed and the corresponding extension tubings may be attached to the inter-connector to receive fluid from the input valve of the inter-connector. A fluid source may then be connected to the input port of the inter-connector and fluids injected into the input port are diverted down the various extension tubings and then into the various lumens within the catheter body.

The output ports of the inter-connector and the proximal end of the tubings may be configured with matching interlocking interface for removable connections. For example, each of the output ports of the inter-connector may be configured with a male Luer Lock interface, while the proximal end of each of the extension tubings may be configured with a female Luer Lock interface. Furthermore, the multi-output inter-connector may be provided with a switch, such that the operator may select "one input one output" mode or "one input multiple outputs" mode. With the selection switch, one would not need the sealing caps to terminate the open output ports when the lumens of the catheter are being used independent of each other for fluid delivery.

Figure 7A:
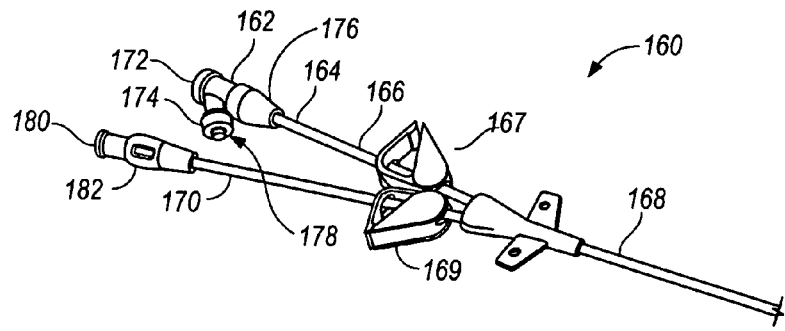
FIG. 7A illustrates another variation of a power injection catheter. The catheter comprises a dual lumen design with the capability for simultaneous high flow injection through the implementation of a bifurcating connector.

FIG. 7A shows one particular variation of a dual lumen (D-shaped) catheter 160 that supports both simultaneous injections through both lumens (e.g., injection of contrast media through both lumens, etc.) for high flow applications, which may be reconfigured for low flow applications where each of the lumens can be used independent of each other for various infusion therapy or blood withdrawal. An inter-connector 162 is constructed to allow independent use of both lumens/extensions where only low flow rate (e.g., about 5 cc/sec or less) is required. As shown in FIG. 7A, a "Y" connector 162 is provided at the proximal end 164 of a first extension leg 166. The lumen of the first extension leg 166 is in fluid communication with one of the two lumens within a main catheter body 168. A second extension leg 170 is provided for delivering fluids into the second lumen within the main catheter body 168. The "Y" connector 162 has an input port 172 and two output ports 174, 176, and the first output port 176 is connected to the first extension leg 166. The second output port 174 is provided with a male Luer Lock interface 178, and the proximal end 180 of the second extension leg 170 is provided with a matching female Luer Lock interface 182. For low flow applications, the second output port 174 may be closed by a cap. Two separate fluid sources may be provided to direct fluids into the two extension legs 166, 170. One may also use one extension leg for blood withdrawal and the other for infusion of medication. A clip 167, 169 may be provided on each of the extension legs 166, 170 to allow the user to selectively close the fluid channel supported by any one of the two extension legs.

Figure 7B:
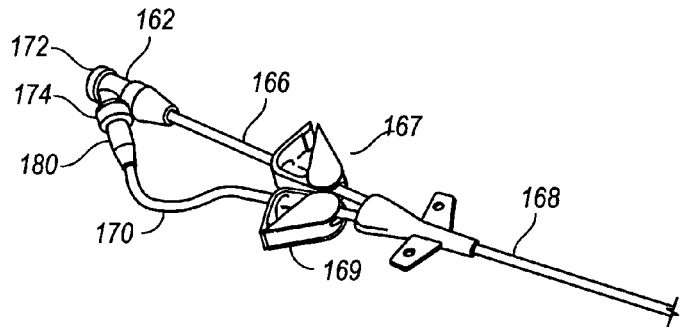
FIG. 7B shows the power injection catheter of FIG. 7A configured for simultaneous high flow injection. The secondary branch is connected to the primary branch through the bifurcating connector.

For high flow applications, one may remove a cap placed on the second output port 174 of the "Y" connector 162, and connect the proximal end 180 of the second extension leg 170 to the second output port 174, as shown in FIG. 7B. In this configuration, fluid injected through the input port 172 of the "Y" connector 162 will flow into both of the extension legs 166, 170 and be directed into both of the lumens within the main catheter body 168, thus allowing simultaneous injection of fluid through both of the lumens. One may also use this configuration to withdraw blood or other fluids from a patient's body through both of the lumens simultaneously. The inter-connector 162 may further be designed to provide equal flow into both of the lumens, such that injection of the fluids through the inter-connector would result in even distribution of pressures into both of the lumens. Once the high flow injection application is accomplished, one may remove/disconnect the second extension leg from the inter-connector and terminate the second output port so that each of the lumens may again be used independently for fluid infusion or extraction.

Figure 8A:
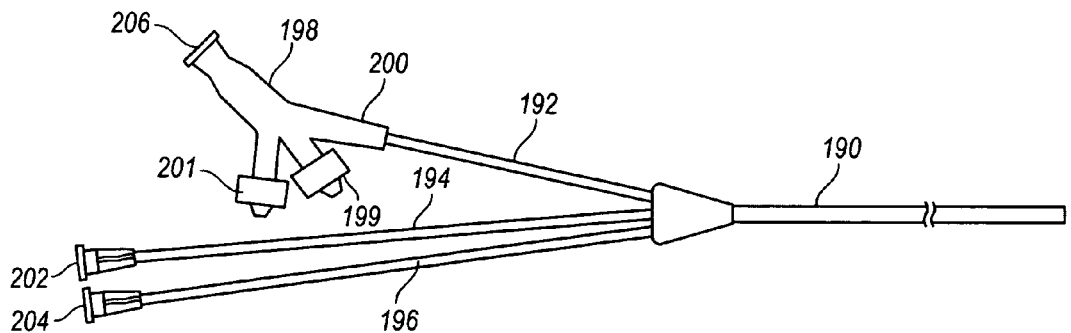
FIG. 8A illustrates yet another variation of a power injection catheter having three lumens. A fluid inter-connector having three output branches is implemented in this variation for simultaneous delivery of fluids into the three separate lumens.

One of ordinary skill in the art having the benefit of the disclosure herein would appreciate that variations of the multi-output inter-connector may be implemented on catheters having three or more lumens to provide the capability for simultaneous injections of a fluid through all the lumens. FIG. 8A illustrates one example where the main catheter body 190 has three lumens, and three extension leg tubings 192, 194, 196 are provided for supplying fluids to each of the lumens. A four-port inter-connector 198 is provided, such that the catheter can be configured for simultaneous injections through all three lumens. In this particular variation, a first port 200 on the inter-connector is connected to the first leg extension 192. Second 199 and third ports 201 are available for connection to the proximal end 202, 204 of the other two leg extension 194, 196. A fourth port 206 is provided for connection to a fluid source. Furthermore, it is contemplated that in another design, the multi-lumen catheter may be configured, such that not all the lumens are implemented for simultaneous injections. For example, in a triple lumen catheter, the inter-connector may only support two extension legs, such that only two of the three lumens are used for simultaneous injections, and the third lumen may be utilized independent of the other two lumens which are linked through the inter-connector.

Figure 8B:
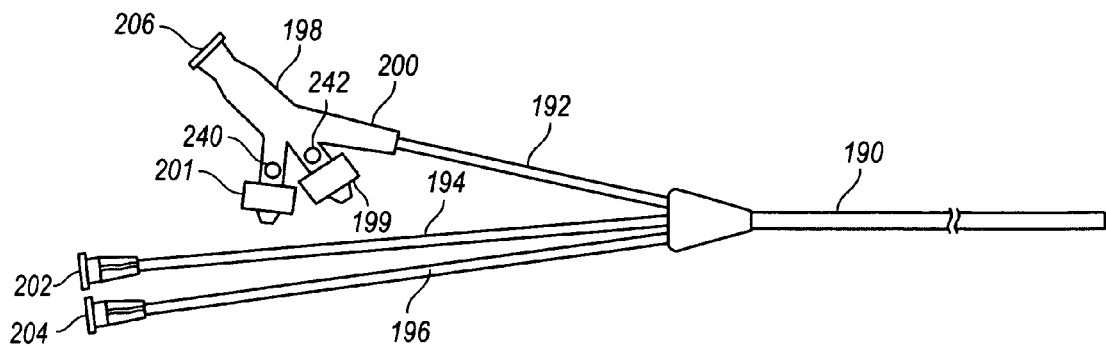
FIG. 8B illustrates another variation of a power injection catheter with gates integrated within the inter-connector to allow the user to open and close selective ports.

In another variation, the "Y" connector 162 further comprises a switch or gate that allows the user to close the additional output port when it is not in use. For example, as shown in FIG. 8B, gates 240 and 242 are provided on the two output ports, 102 and 199 respectively. When the two output ports 201, 199 are not in use, the use may close them so that the leg extension 192 connected to the inter-connector 198 may be used independently for fluid infusion or aspiration.

Figure 9:
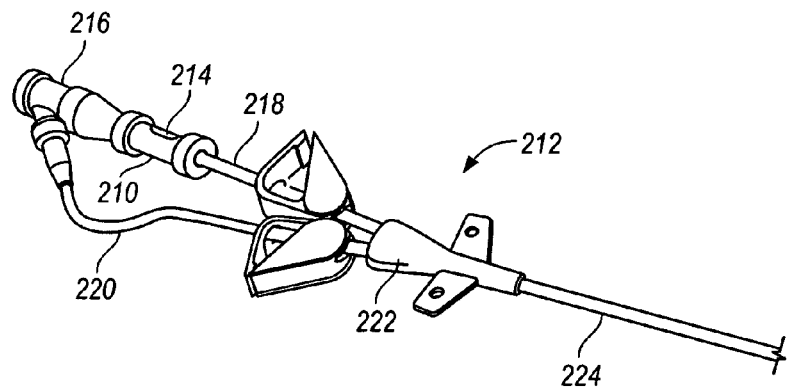
FIG. 9 illustrates another variation of a power injection catheter with a built-in pressure relief mechanism. In this variation, the pressure relief mechanism is integrated into one of the extension arms.

In another variation, a pressure relief mechanism (e.g., balloon, diaphragm, burst disk, pressure relief valve, etc.) 210 may be implemented on the multi-lumen catheter with simultaneous injection capability 212. For example, as shown in FIG. 9, a balloon 214 may be integrated into the inter-connector (i.e., "Y" connector) 216 of a dual lumen catheter. In another variation, a pressure relief valve may be design into the inter-connector 216. It is also contemplated that the pressure relief mechanism may be built into either of the extension legs 218, 220. One may also place the pressure relief mechanism in the bifurcation 222, which provides the branching to the two extension legs 218, 220. In addition, pressure relieving mechanism may also be integrated directly into the main catheter body 224.

Figure 10:
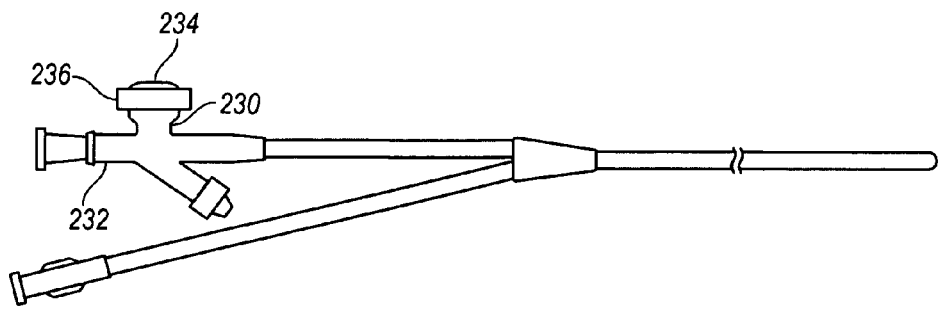
FIG. 10 illustrates another variation of a power injection catheter with a pressure relief mechanism implemented on a side branch of the fluid inter-connector.

FIG. 10 illustrates one variation where an additional branch 230 is provided on the inter-connector 232 for supporting a pressure relief mechanism 234. In this particular variation, the branching 230 is configured to receive a housing 236 with an embedded balloon 234. The housing 236 may be configured as a removable cap so that the balloon can be easily replaced. A burst disk may also be integrated within the housing 236 such that the pressure relief mechanism (i.e., the balloon) only activates when the pressure inside the inter-connector 232 exceeds the pressure threshold and compromises the burst disk. In another variation, the housing 236 may simply comprise a burst disk without an additional pressure relief mechanism. One of ordinary skill in the art having the benefit of this disclosure would appreciate that the inter-connector may be configured with both the fluid port control gate and the pressure relief mechanism.

In yet another variation, an additional inter-connector with built-in pressure relief mechanism, such as the ones shown in FIG. 2A, 2B, 3B, 5A, 6A, may be attached to either the input port or one of the output ports of the "Y" connector to provide the pressure relieving capability to the multi-lumen catheter, such as the one shown in FIG. 7A. For example, the dual lumen catheter of FIG. 7A may be provided with pressure relieving capability by adding an inter-connector, with a built-in pressure relief mechanism, to the input port of the "Y" connector. In another design, the device shown in FIG. 9 may comprise three detachable parts: (1) a dual lumen catheter with two leg extensions, (2) a "Y" connector inter-connector, and (3) an inter-connector with a built-in pressure relief mechanism. Each of the three parts is configured with a connection interface for forming the desired device. Because each of the three parts is removable from the device, if one of the parts malfunctions, the operator may replace the specific malfunctioning part without replacing the whole device.

The multi-lumen catheter with simultaneous-injection capability may be inserted into patients through various catheter placement procedures that are well known to one of ordinary skill in the art. For example, the multi-lumen catheter may be inserted through a vein in the patient's arm. Once the catheter is inserted, the distal portion of the catheter may be threaded up the vessel toward the heart. In one variation, the distal tip of the catheter is placed within the patient's superior vena cava. Once the catheter is secured in place, the physician may then utilize the individual fluid paths provided by the multi-lumen for injection of fluids, medication, or nutrients. The physician may also use one or more of the lumens to withdraw blood from the patient's circulatory system. For high flow rate power injection applications, the physician may configure the power injection catheter by connecting all the extension legs to the inter-connector and simultaneously inject fluids into all the lumens in the catheter from a single fluid source. Once the power injection is completed, the physician may reconfigure the extension legs for individual infusion.

Figure 11A:
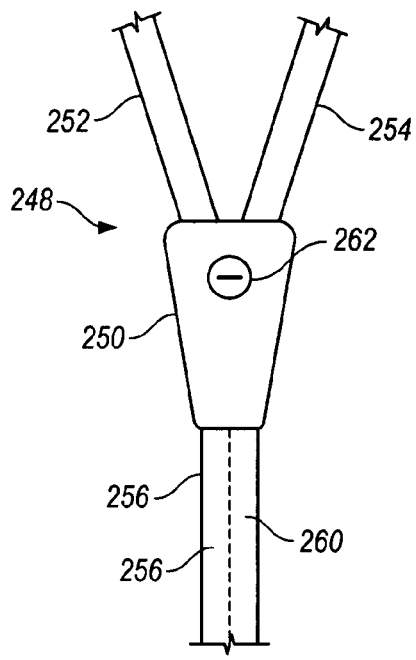
FIG. 11A illustrates one variation of a bifurcating catheter with an integrated valve within the bifurcation to control fluid flow between the two fluid channels within the catheter. The valve is shown in the open position to allow fluid communication between the two channels.
Figure 11B:
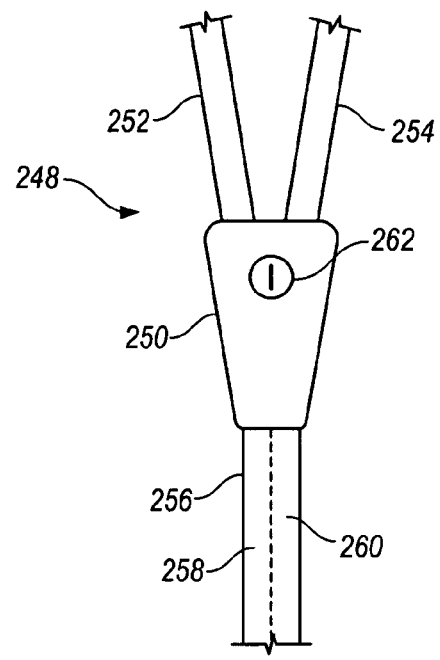
FIG. 11B illustrates the bifurcating catheter of FIG. 11A with the valve in the closed position preventing fluid flow between the two fluid channels.

In another variation, a multi-lumen catheter is configured with one or more valves such that fluid communication is established between the various lumens within the catheter. Referring to FIG. 11A, one variation of a dual lumen catheter 248 with bifurcating arms 252, 254 is configured with a valve 262 on the bifurcation 250. The valve may be a stop-cock like device molded into the catheter bifurcate. When the valve is turned horizontally, as shown in FIG. 11A, fluids can flow between the first lumen 258 and the second lumen 260. When the valve is turned vertically, as shown in FIG. 11B, the two lumens are separated, and each of the lumens can be utilized for independent fluid delivery. As one of ordinary skill in the art would appreciate, various other valves may also be implemented to provide user control of fluid flow between the two adjacent lumens within the catheter.

Figure 12:
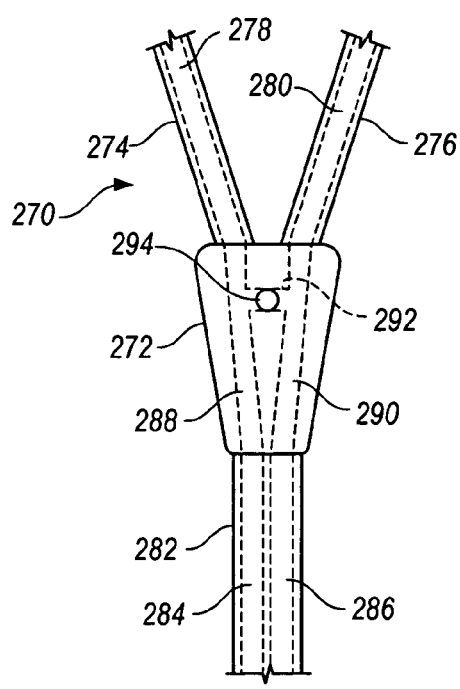
FIG. 12 illustrates another variation of a bifurcating catheter with a pressure driven valve positioned within the bifurcation to permit fluid communication between the two fluid channels supported by the catheter.

In another variation, a pressure driven valve may be implemented between the plurality of lumens within a multi-lumen catheter. For example, as shown in FIG. 12, a valve 294 that opens at a pre-designated pressure (i.e., a pop-valve, etc.) can be implemented within the bifurcation 272 to allow fluid flow between the two lumens 288, 290 within the dual lumen catheter 270. The valve maintains the closed position when pressure gradient between the two lumens 288, 290 is below a predetermine level. The valve opens when the pressure gradient exceeds a pre-designated pressure and allows the fluid to flow from one lumen to the other. In one application, the user injects fluids through the first extension leg 274 and fluids flow from the first lumen 278 through the corresponding lumen 288 within the bifurcation into the first lumen 284 within the dual lumen catheter 282 when the injection pressure is below the pre-designated pressure. When the pressure within the first lumen 288 exceeds the pre-designated pressure, the valve 294 opens and allows fluid to flow into the second lumen 290 in the bifurcation. The proximal end of the second extension leg may be closed such that fluid entering the second lumen 290 may be directed into the second lumen 286 within the dual lumen catheter 282.

In one variation, the valve is configured to open when the pressure gradient across the valve is above the pressure required for typical medication infusion (e.g., below 60 psi.). Either a unidirectional valve or a bidirectional valve may be utilized depending on the particular application. In one configuration, a bidirectional valve is used, such that excessive pressure can be shunted to the adjacent lumen in either direction. The bidirectional valve may also normalize the pressure between two lumens when both of the extension legs 274, 276 are utilized simultaneously for fluid injection. When the pressure within either one of the lumen 278 or 280 is greater then the pressure within the adjacent lumen by a pre-determined amount, the bidirectional valve would open and allow the pressure between the two lumens 278, 280 to normalize. In another variation, two valves are placed between the two lumens 288, 290, such that one valve would open when the first lumen 288 is overpressurized, while the other valve would open when the second lumen 290 is overpressurized.

In yet another variation, the valve mechanism is integrated within an adaptor coupled to a multi-lumen catheter to permit fluid communication between the lumens of the catheter. The valve mechanism may comprise a manual valve that allows the user to control the fluid flow between the lumens. In another variation, the valve mechanism comprises a pressure valve. For example, the valve may be configured with a pre-defined threshold value, such that when the pressure within one lumen of the catheter exceeds the pressure within an adjacent lumen of the catheter by the predefined amount, the valve opens up and relieves pressure within the lumen with the higher pressure. The valve in the adapter may be a bidirectional valve or a unidirectional valve.

Figure 13:
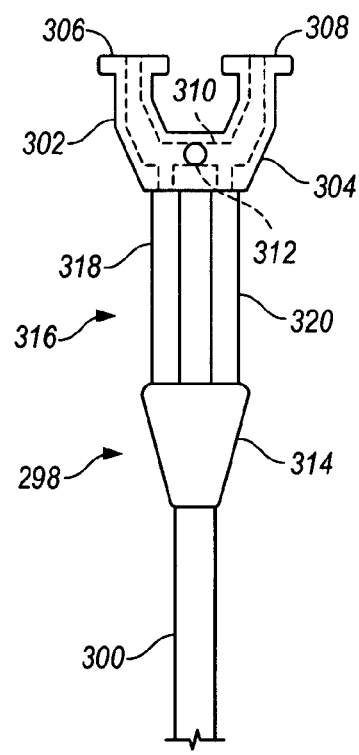
FIG. 13 illustrates another variation where an adaptor including a valve is attached to a bifurcating catheter to provide fluid communication between the fluid channels supported within the bifurcating catheter.

In one example, a luer connection 302 on a bifurcating catheter 298 is provided with a valve mechanism 312, as shown in FIG. 13. The bifurcating catheter 298 comprises a dual lumen catheter 300 with a bifurcation 314 supporting two bifurcating branches 318, 320, each of which connects to the luer connection 302. The luer connection 302 comprises two locking interfaces 306, 308 which may be utilized for connection to a fluid source, a suction source, or other catheters. A valve 312 is provided in the channel 310 connecting the two lumens within the luer connection 302.

In another example, the bifurcating branches 318, 320 are provided with luer interfaces on their proximal ends. An adapter, similar to the luer connector 302 shown in FIG. 13, is provided for connection to the two bifurcating branches 318, 320 through the luer interfaces on the bifurcating branches. The distal end of the adaptor may be provided with matching interfaces to receive the two bifurcating branches. Once the adapter is connected to the bifurcating catheter, a structure similar to the one shown FIG. 13 is formed.

In yet another example, the proximal end of a dual lumen catheter is connected directly onto a luer connector similar to the one 302 shown in FIG. 13. Additional tubings may be connected to the luer interfaces 306, 308 to infuse fluid into the dual lumen catheter. The built-in valve in the luer connection modulates fluid flow between the two lumens within the dual lumen catheter. One of ordinary skill in the art having the benefit of this disclosure would appreciate that luer connectors or adaptors with an integrated valve supporting inter-lumen fluid communication may be configured to support catheters with three or more lumens.

Figure 14:
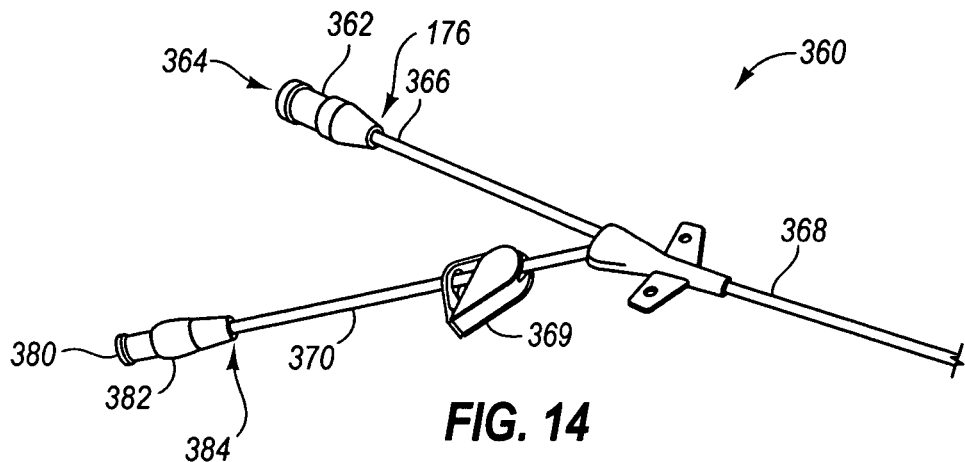
FIG. 14 shows one embodiment of a power injection catheter including a proximal valve structure.

A further aspect of the instant disclosure relates to a power injection catheter for high flow rate delivery of fluids, the power injection catheter including a single lumen. In further detail, a power injection catheter including a single lumen may comprise a proximal end region with two extension tubes in communication with the lumen of the catheter. Further, one extension tube of the two extension tubes may be configured for power injection and the other extension tube may include a proximal valve configured for performing infusion or aspiration processes. For example, FIG. 14 shows one particular embodiment of a single lumen catheter 360 configured for relatively high-flow infusion (e.g., at a flow rate of at least about 3 cubic centimeters per second) or "power injection" through its lumen. In one example, injection of a contrast media for vascular imaging (computed tomography, magnetic resonance imaging, etc.) may be accomplished. Of course, the single lumen catheter 360 may also be employed for low-flow applications, if desired, or other for various infusion therapies or blood withdrawal. As shown in FIG. 14, a connector 362 is provided with an input port 364 and an output port 176 communicating with the first extension tube 366. The lumen of the first extension tube 366 is in fluid communication with the lumen within a main catheter body 368. Further, connector 362 of first extension tube 366 may be configured for delivering fluids into the lumen of the catheter 360 at relatively low flow rates (e.g., less than about 3 cc per second). In addition, generally, a bidirectional valve or so-called proximal valve, as known in the art, may be incorporated within connector 362 of catheter 360. Catheter 360 also includes a second extension tube 370 with a connector 382 configured for delivering fluids into the lumen of the catheter 360 at relatively high flow rates. Accordingly, for example, connector 382 may include an input port 380 and an output port 384 configured for performing power injection. Tubing clamp 369 may be provided on extension tube 370 to allow the user to selectively close the fluid channel of extension tube 370.

Figure 15:
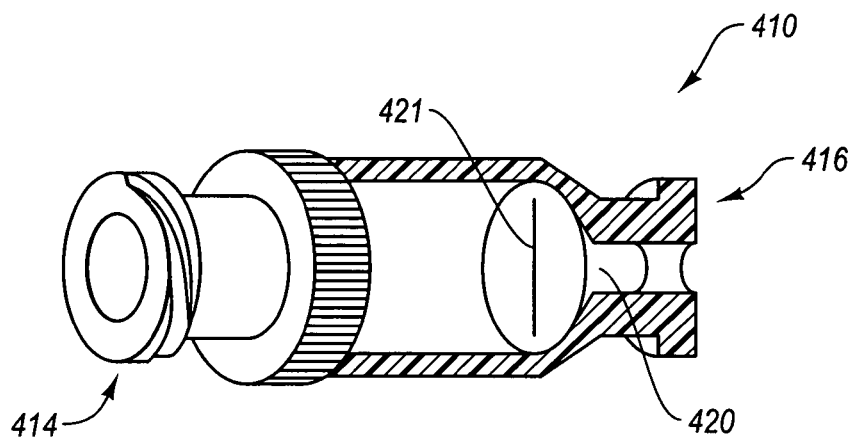
FIG. 15 shows a schematic view of one embodiment of a proximal valve structure.

A proximal valve incorporated in connector 362 may be configured to allow for infusion or aspiration therethrough. For example, U.S. Pat. Nos. 5,169,393, 5,201,722, 5,205,834, 5,843,044 and 5,984,902, the disclosure of each of which is incorporated herein, in its entirety, by this reference, each discloses a pressure-responsive, bidirectional valve. Generally, such a proximal valve may comprise a deformable body including a passageway extending through at least a portion of the deformable body. More particularly, FIG. 15 shows a schematic embodiment of a valve structure 410 including a deformable element 420 including a slit 421 extending through the deformable element 420. As may be appreciated, deformable element 420 may embody various structures and shapes.

As shown in FIG. 15, in one embodiment, deformable element 420 may comprise a plug that substantially fills a portion of the lumen formed between the proximal end 414 and distal end 416 of the valve structure 410. As shown in FIG. 15, valve structure 410 may be "normally-closed" in both directions of flow through the valve. Explaining further, deformable element 420 may be configured (e.g., at least partially compressed or otherwise structured) to resist flow through the slit 421 for pressure a differential existing between (i.e., in either direction) the distal end 416 and proximal end 414 of the valve structure 410. Put another way, valve structure 410 may be configured so that a pressure differential must exceed a selected normally-closed aspiration pressure differential limit to cause aspiration through the slit 421 of the deformable element 420 of the valve structure 410. Similarly, valve structure 410 may be configured so that a pressure differential must exceed the selected normally-closed infusion pressure differential limit to cause infusion through the valve structure 410. As known in the art, the respective pressure differentials for causing infusion or aspiration, respectively, may be different and may be, optionally, adjustable.

Figure 16:
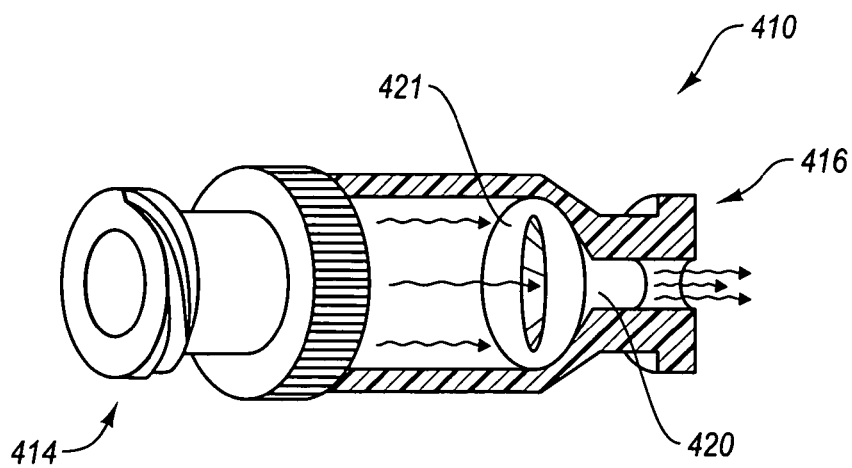
FIG. 16 shows a schematic view of the proximal valve structure shown in FIG. 15, when used for infusion.
Figure 17:
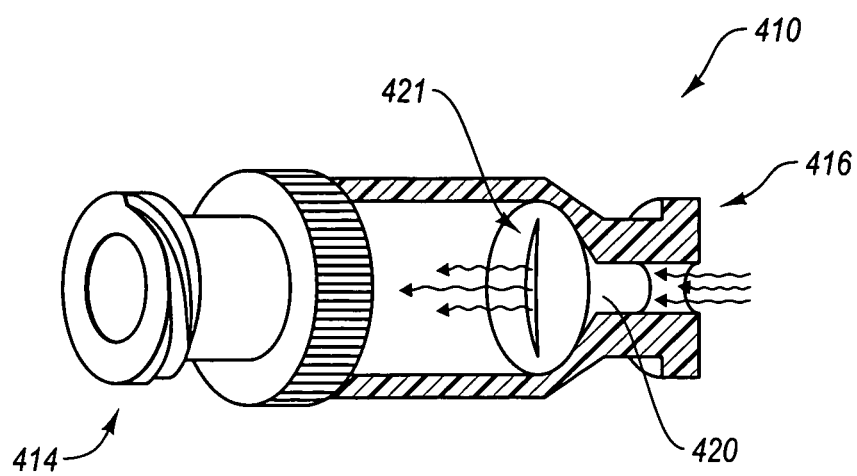
FIG. 17 shows a schematic view of the proximal valve structure shown in FIG. 15, when used for aspiration.

As shown in FIG. 16, in a schematic view of valve structure 410 during use, a selected pressure differential (i.e., wherein a pressure developed on the proximal end 414 of the deformable element 420 exceeds a pressure developed on the distal end 416 of the deformable element 420) that exceeds the selected normally-closed infusion pressure differential limit may cause the slit 421 to open and provide a passageway for fluid to pass through in a direction from the proximal end 414 to the distal end 416. Similarly, as shown in FIG. 17 in a schematic view of valve structure 410, a selected pressure differential (i.e., wherein a pressure developed on the distal end 416 of the deformable element 420 exceeds a pressure developed on the proximal end 414 of the deformable element 420) that exceeds a selected normally-closed aspiration pressure differential limit may cause the slit 421 to open and provide a passageway for fluid to pass through in a direction from distal end 416 to proximal end 414. Such a proximal valve may allow for ease of use of the catheter 360.

Figure 18:
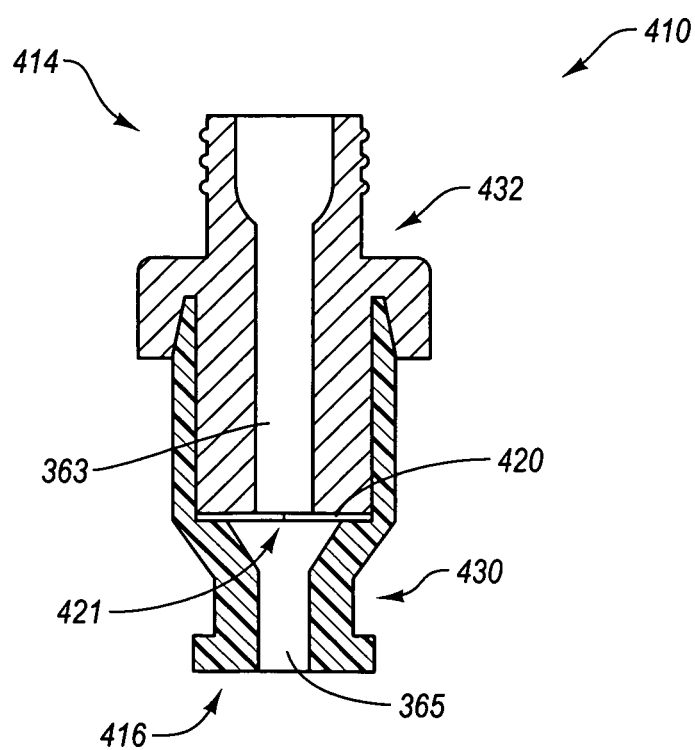
FIG. 18 shows a schematic of a second embodiment of a proximal valve structure.

In further detail, FIG. 18 shows another embodiment of valve structure 410 including a deformable element 420 comprising a deformable disk with a slit 421 formed through the deformable disk. In addition, as shown in FIG. 18, deformable element 420 is positioned between a proximal body portion 432 and a distal body portion 430. Thus, valve structure 410 may be assembled as follows: deformable element 420 may be positioned within distal body portion 430, proximal body portion 432 may be positioned as shown in FIG. 18, and distal body portion 430 and proximal body portion 432 may be affixed to one another by an adhesive, solvent welding, thermal bonding, or as otherwise known in the art. Of course, any other embodiments of deformable element may be employed to form a proximal valve, without limitation.

Figure 19:
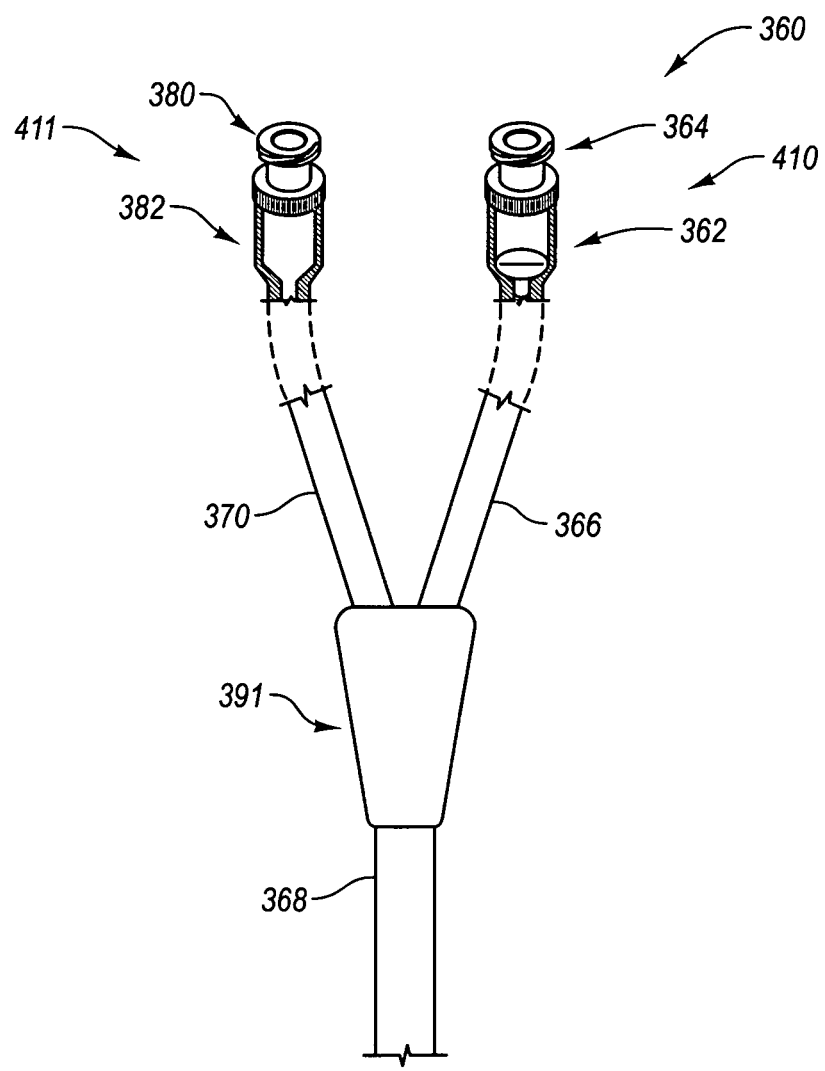
FIG. 19 shows a schematic view of the power injection catheter shown in FIG. 14.

FIG. 19 shows a schematic view of catheter 360 including a proximal valve structure as shown in FIGS. 15-18 incorporated within connector 362. Accordingly, it may be appreciated that, for relatively low-flow applications, optionally, extension tube 370 (i.e., input port 380) may be capped and extension tube 366 (i.e., input port 364 of connector 362) and may be used for infusion or aspiration. For relatively high-flow applications, optionally, extension tube 366 (i.e., input port 364 of connector 362) may be capped and input port 380 of connector 382 may be used for power injection. More particularly, for high flow applications, one may remove a cap placed on the input port 380 and connect a fluid source to input port 380. Such a high flow application may flow fluid through catheter 360 at a rate of at least about 3 cc per second; optionally, a fluid may flow through catheter 360 at a rate of at least 5 cc per second. In this configuration, fluid injected through the input port 380 will flow into extension tube 370 and be directed into the lumen within the main catheter body 368 of catheter 360. As mentioned above, the second output port 382 may be configured for relatively high-flow applications. Thus, a fluid source may be provided to communicate fluid into the extension tube 370. Of course, one of extension tubes 366, 370 may be used for blood withdrawal and the other for infusion of medication. Also, a pressure relief device or mechanism as described above may be incorporated into the catheter 360. For example, a pressure relief or buffering device, such as an accumulator (e.g., a piston-type or bladder-type accumulator), pressure relief valve, burst disc, or other device configured to buffer, ameliorate, or reduce pressure fluctuations or pressure within a lumen may be included by catheter 360 as described above or as otherwise known. Of course, input port 380 may be used to withdraw blood or other fluids from a patient's body through the lumen within the main catheter body 368 of catheter 360, if desired.

Figure 20:
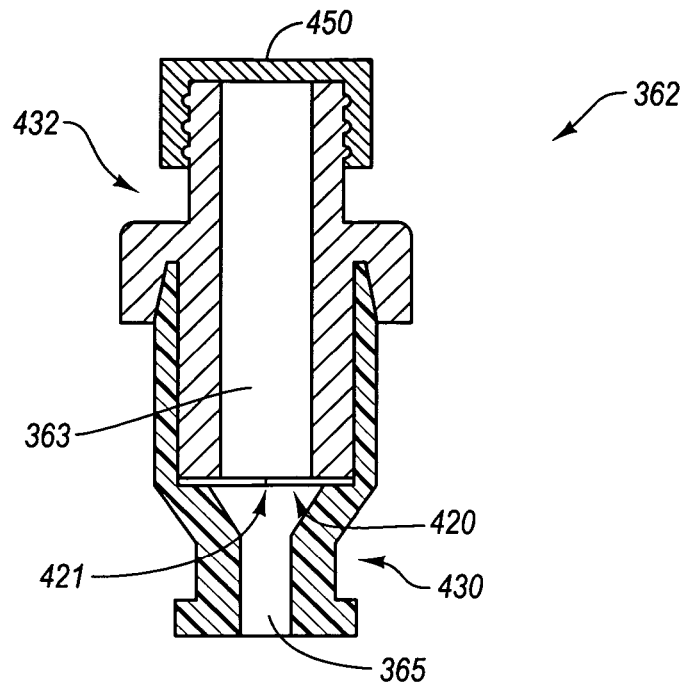
FIG. 20 shows a schematic view of a connector of a power injection catheter including a proximal valve structure and a cap assembled to an input port of the proximal valve structure.
Figure 21:
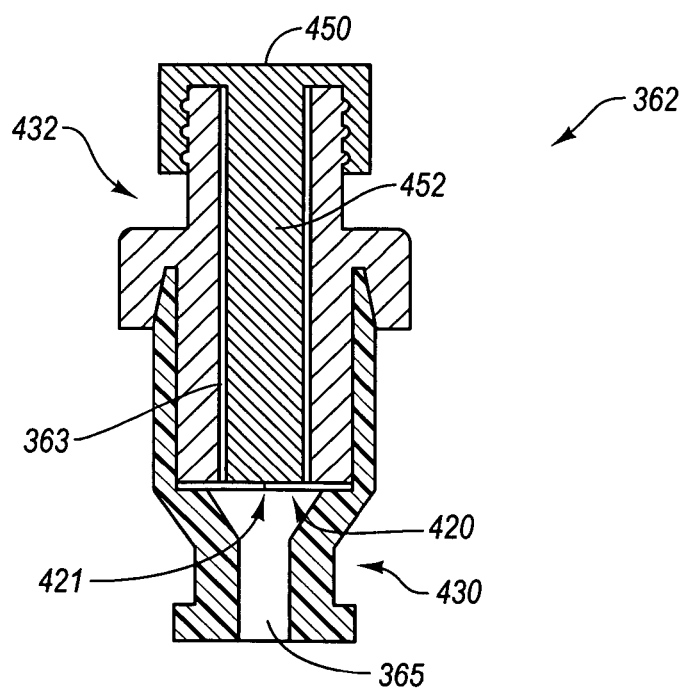
FIG. 21 shows a schematic view of a connector of a power injection catheter including a proximal valve structure and a different embodiment of a cap assembled to an input port of the proximal valve structure.

As may be appreciated, use of one extension tube of a single lumen catheter may cause another extension tube of the catheter to become pressurized. Further, if a proximal valve is in a configuration included within such a pressurized extension tube, leaking of a fluid through the proximal valve or damage to the proximal valve may occur. Accordingly, the instant disclosure contemplates that a proximal valve may be selectively isolated from an extension tube used for power injection or may be otherwise configured to prevent leakage from the proximal valve or damage to the proximal valve. For example, a proximal valve may be configured to withstand the increases in pressure (e.g., of up to about 300 psi) within a lumen of a catheter during power injection without damage. In another embodiment, a proximal valve may be pressurized, but fluid flow through the extension tube including the valve may be at least substantially prevented. In another example, a tubing clamp (removable or nonremovable) may be used to seal or close the extension tube communicating with the connector including the proximal valve. In a further embodiment, a cap may be assembled to the connector of the extension tube including the proximal valve to prevent leakage through the proximal valve. For example, FIG. 20 shows a schematic view of a connector 362 including a proximal valve structure 410, wherein a cap 450 is assembled to input port 364. Thus, pressure developed within bore 365 of the distal end of connector 362 may communicate through the slit 421 formed in deformable element 420 to pressurize cavity 363. Also, deformable element 420 may be positioned between a proximal body portion 432 and a distal body portion 430. In another embodiment, deformable element 420 may be affixed between bore 365 and cavity 363 (e.g., by adhesive or as otherwise known in the art). Of course, as the pressure within bore 365 is reduced below the pressure within cavity 363, fluid may pass through the slit 421 formed in deformable element 420 as described above. Cap 450 may be coupled to port 364 by threads (e.g., a luerlock connection) or as otherwise known in the art. Optionally, a sealing element (e.g., an O-ring) may be positioned between cap 450 and input port 364 to provide a seal that is maintained for pressures below an anticipated maximum pressure developed within cavity 363. FIG. 21 shows another embodiment of connector 362 including a cap 451 coupled to input port 364. As shown in FIG. 21, cap 451 includes a support element 452 extending from a distal end of cap 450 and into cavity 363 or connector 362. Also as shown in FIG. 21, support element 452 may be configured to contact the deformable element 420 along surface 453 of support element 452. Such a configuration may resist against movement of the deformable element 420 in a direction toward input port 364. Such a configuration may support deformable element 420 to prevent damage or may seal the slit 421 of the deformable element 420 so that fluid does not pass through the slit 421 when pressure is developed in bore 365. Thus, in one embodiment, cavity 363 may be allowed to pressurize in response to pressure developed within bore 365, as described above in relation FIG. 20. In another embodiment, contact between surface 453 of support element 452 and deformable element 420 may be configured to prevent pressurization of cavity 363. Explaining further, support element 452 may be configured to cause the slit 421 formed in deformable element 420 to remain closed against an anticipated maximum pressure developed within bore 365. Of course, optionally, a tubing clamp that can be removable may be closed to prevent fluid communication between the connector 362 and the lumen of the catheter to which it is connected.

Furthermore, it may be appreciated that a selection valve element may be configured to selectively allow fluid communication through one or more extension tubes of a plurality of extension tubes which are capable of fluid communication with a main catheter. More particularly, such a selection valve element may be configured to normally allow fluid communication between a main catheter and at least one extension tube including a proximal valve. However, when it is desired to perform a power injection the selection valve element may be configured to allow for fluid communication with at least one extension tube configured for power injection while simultaneously preventing (or at least substantially preventing) fluid communication with one or more extension tubes including a proximal valve. Such a selection valve element may embody a manual valve or an automatic valve, without limitation. Furthermore, such a selection valve element may include a plurality of components including one or more or the following: a check valve, a poppet valve, a ball valve, a shuttle valve, a spool valve, a solenoid valve, and any other suitable valve.

Figure 22:
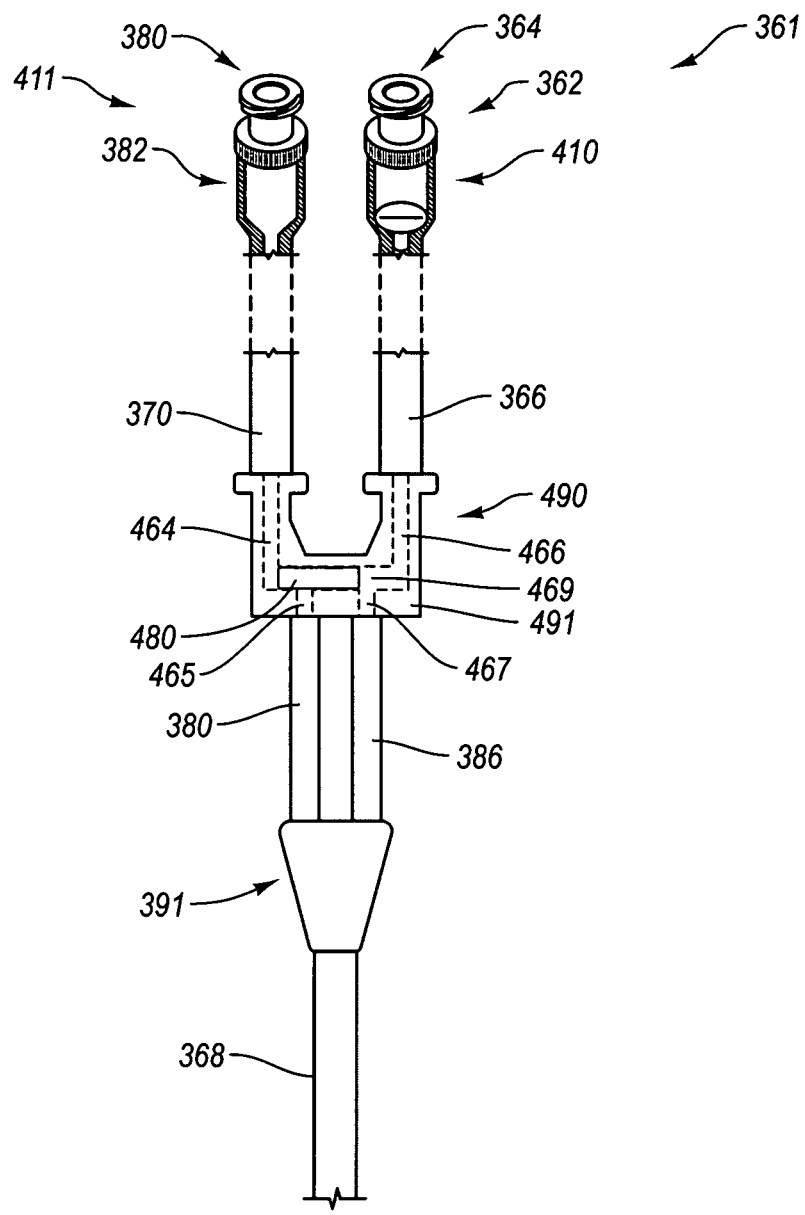
FIG. 22 shows a partial schematic view of a power injection catheter including a selection valve mechanism configured to selectively control fluid communication between two extension tubes and the lumen of a single lumen catheter, one extension tube including a proximal valve and one extension tube configured for power injection.
Figure 23:
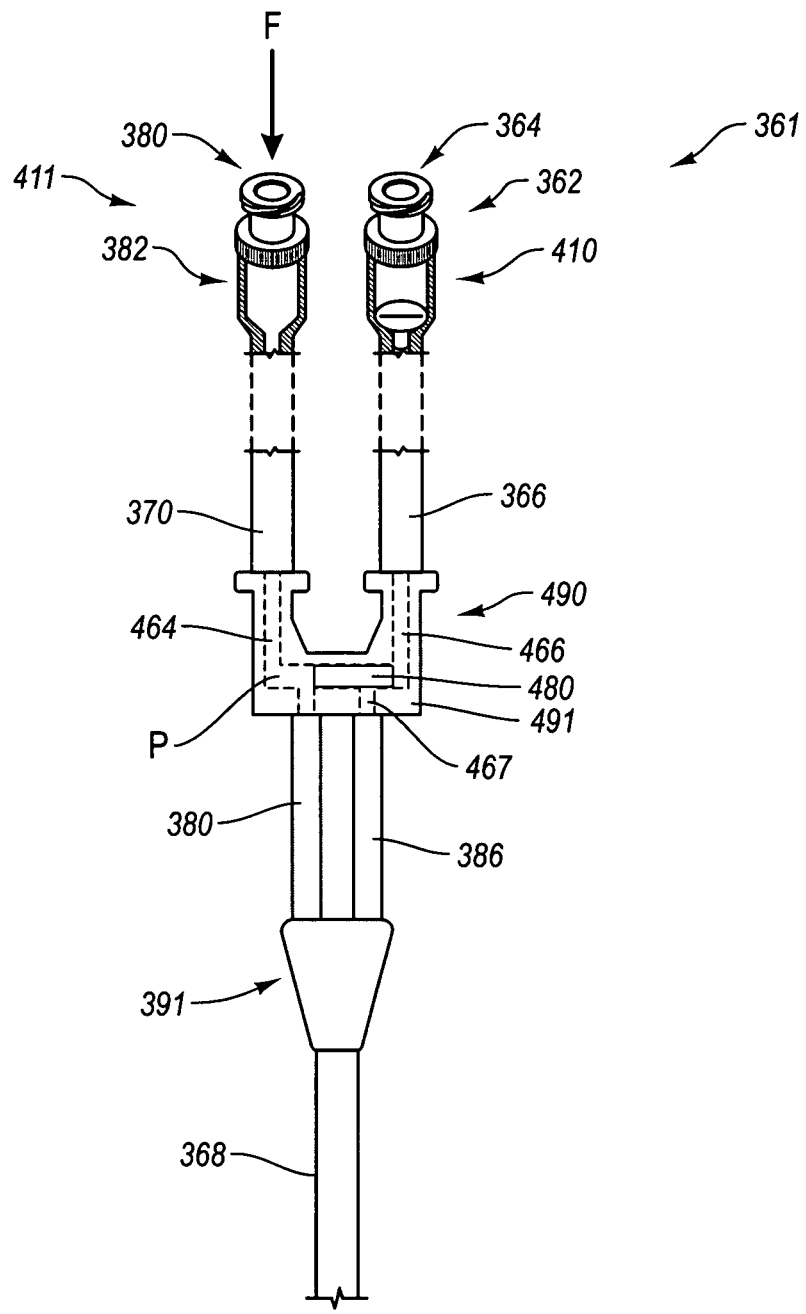
FIG. 23 shows the power injection catheter shown in FIG. 22, during power injection.

For example, FIG. 22 shows a partial schematic view of a catheter 361 including a selection valve mechanism 490 configured to selectively control fluid communication between extension tubes 366, 370 and the lumen of catheter 368. Explaining further, selection valve mechanism 490 includes a shuttle element 480 that is positional to selectively prevent fluid communication between the lumen of catheter body 368 and one of extension tubes 366, 370, while allowing fluid communication with one of extension tubes 370, 366. As shown in FIG. 22, selection valve mechanism 490 may include a body 491 which defines inlet lumens 464 and 466. In addition, shuttle element 480 may be positioned in a passageway extending between inlet lumens 464 and 466 and the passageway may also be connected to outlet lumens 465 and 467. Shuttle element 480 may be configured so that a first position of shuttle element 480 within passageway 469 allows fluid communication between extension tube 366 and the lumen of catheter body 368 (i.e., through inlet lumen 466, a portion of passageway 469, and outlet lumen 467). Further, as known in the art, shuttle element 480 may be biased (e.g., by a biasing element) to occupy the first position, as shown in FIG. 22. Such a configuration may allow for the proximal valve structure 410 within connector 362 to normally be in fluid communication with the lumen of catheter body 368. However, as shown in FIG. 23, when extension tube 370 is used for power injection or any other infusion process that is not compatible with proximal valve structure 410, pressure P may be developed within the inlet lumen 464 and passageway 469 of a sufficient magnitude to move shuttle element 480 to a second position. Thus, such a second position may prevent fluid communication between extension tube 366 and the lumen of catheter body 368 and may allow fluid communication between extension tube 370 and the lumen catheter body 368. As known in the art, shuttle element 480 may comprise a substantially spherical ball. Further, any shuttle-type or other selection valve mechanism, as known in the art may be employed to selectively control fluid flow between a plurality of extension tubes and at least one lumen of a catheter. Such a configuration may provide a relatively robust, simple, and automatic valve mechanism for selectively controlling fluid communication between extension tubes 370, 366 and the lumen of catheter body 368. In addition, any selection valve mechanism (e.g., automatic or manual) may be employed between an extension tube including a proximal valve and at least another extension tube of a catheter capable of power injection.

Figure 24:
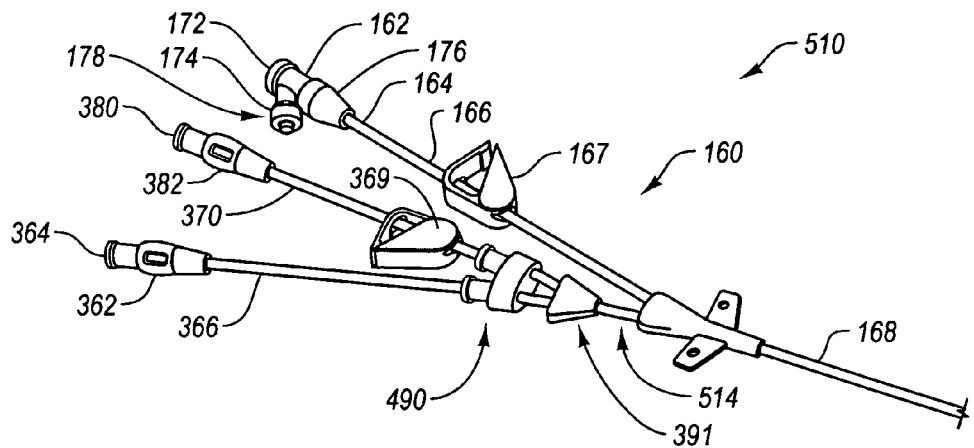
FIG. 24 shows perspective view of a power injection catheter comprising a main catheter including two lumens and two main extension tubes, wherein one main extension tube is bifurcated into two secondary extension tubes, one secondary extension tube including a proximal valve and one secondary extension tube configured for power injection.
Figure 25:
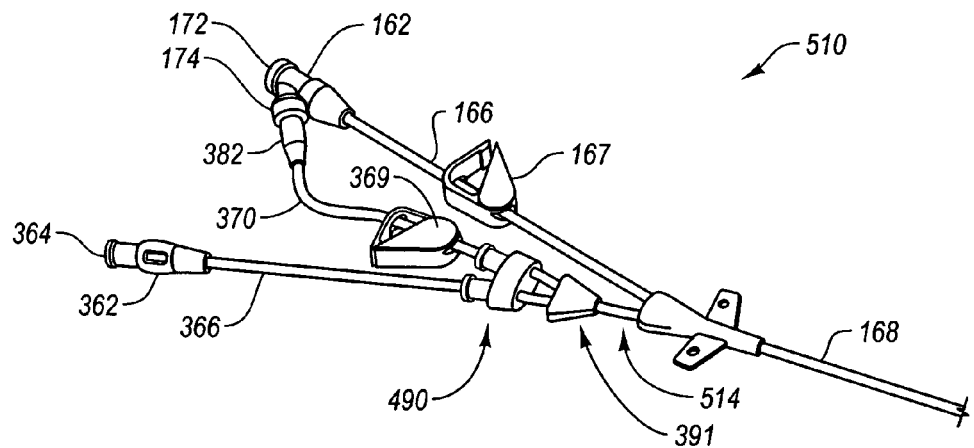
FIG. 25 shows a perspective view of the power injection catheter shown in FIG. 24, configured for power injection.

The instant disclosure also contemplates that a catheter including more than one lumen may include at least one extension tube including a proximal valve and at least one extension tube configured for power injection. For example, FIG. 24 shows a perspective view of a catheter 510 including an intra-connector as discussed above. More specifically, catheter 510 includes a main extension tube 166 in fluid communication with a first of two lumens within a main catheter body 168 and another main extension tube 514, which is in fluid communication with a second of the two lumens within the main catheter body 168. Furthermore, main extension tube 514 may be coupled to secondary extension tube 366 and secondary extension tube 370 through selection valve mechanism 490, which is optional. Put another way, main extension tube 514 may be operably coupled to the catheter structure generally as shown in FIGS. 21 and 22. Selection valve mechanism 490 may be configured to selectively allow fluid communication between one of secondary extension tubes 366 and 370 and the second lumen of the two lumens within the main catheter body 168. In another embodiment, during power injection, selection valve mechanism 490 may be omitted and connector 362 may be optionally capped, or otherwise isolated, during power injection, as discussed and shown with respect to FIGS. 20 and 21. Further, as discussed above, connector 362 may include a proximal valve, which may allow for infusion or aspiration through one lumen of the two lumens within main catheter body 168. As shown in FIG. 25, for high-flow applications (i.e., power injection), second output port 174 of connector 162 may be connected to the proximal end 380 of connector 382. In this configuration, fluid injected through the input port 172 of the connector 162 will flow into both of the main extension tubes 166 and 514 and be directed into both of the lumens within the main catheter body 168. Thus, simultaneous injection of fluid through both of the lumens of main catheter body 168 may be accomplished. During such high-flow application, the selection valve mechanism 490 may prevent fluid communication between secondary extension tube 366 and main extension tube 514, to prevent leakage from or damage to a proximal valve within connector 362. Of course, such a configuration may be employed to withdraw blood or other fluids from a patient's body through both of the lumens of main catheter body 168 simultaneously, if desired. Once the high-flow injection application has been accomplished, extension tube 370 may be disconnected from the second output port 174 and selection valve mechanism 490 may be moved or biased so that one lumen of the main catheter body is in fluid communication with the proximal valve positioned within connector 362 and the other lumen of main catheter body 168 is in fluid communication with connector 162 of main extension tube 166.

Figure 26:
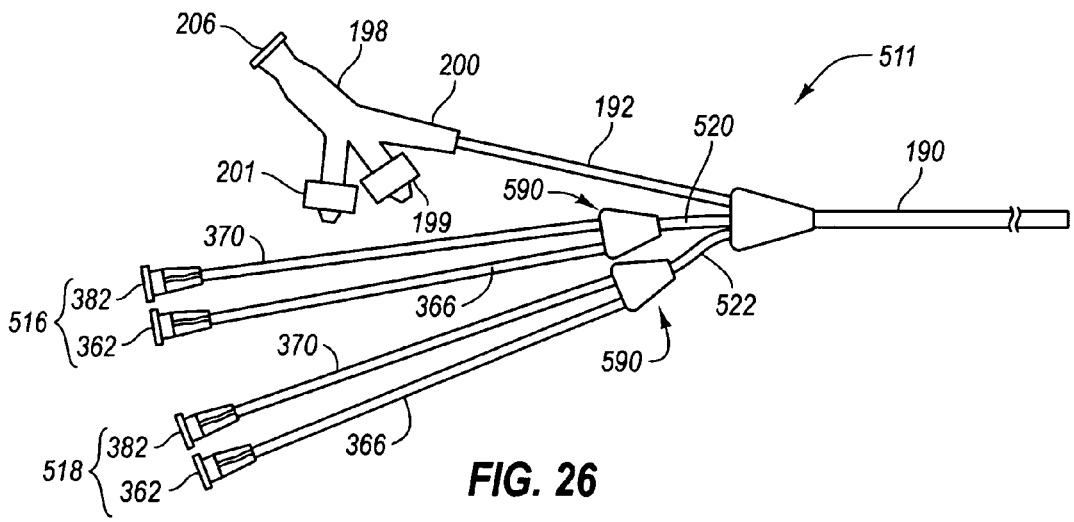
FIG. 26 shows a perspective view of a power injection catheter comprising a main catheter including three lumens and three main extension tubes, wherein two main extension tubes are bifurcated into respective pairs of secondary extension tubes, one of each pair of secondary extension tubes including a proximal valve and one of each pair of secondary extension tubes configured for power injection.

In addition, one may appreciate that variations of the catheter embodiment described above with respect to FIGS. 23 and 24 may be implemented on catheters including three or more lumens. For example, FIG. 26 shows a schematic view of a catheter system 511 including a main catheter body 190 that includes three lumens. Further, catheter system 511 includes three main extension tubes 192, 520, and 522, which are in fluid communication with each of the lumens of the main catheter body 190, respectively. A four port connector 198 is configured to allow simultaneous injections through all three lumens of main catheter body 190. More particularly, connector 198 includes extension tube 192 connected thereto via port 200, a port 199, and another port 201. Port 199 and port 201 may be connected to connectors 382 of each of secondary extension tubes assemblies 516 and 518, respectively. Each of secondary extension tube assemblies 516 and 518 may include secondary extension tubes 366 and 370 optionally connected to a selection valve mechanism 590, wherein selection valve mechanism 590 is configured to selectively allow one of secondary extension tubes 366 and 370 to communicate with main extension tubes 520 or 522, respectively. In another embodiment, selection valve mechanisms 590 may be omitted and connectors 362 of secondary extension tubes 366 may be capped or otherwise isolated during power injection, as described with respect to FIGS. 20 and 21. Of course, any of ports 206, 380, or 364 may be used for infusion or aspiration, as may be desired. Thus, in summary, one or more of main extension tubes 192, 520, and 522 may be employed for performing a power injection or another high flow application (e.g., having a flow rate of at least about 3 cc per second), without limitation.

One skilled in the art will appreciate that aspects of the instant disclosure can be practiced by other than the described embodiments, which are presented for purposes of illustration and not of limitation, and the instant disclosure is limited only by the claims which follow. Put another way, while certain embodiments and details have been included herein for purposes of illustration, it will be apparent to those skilled in the art that various changes in the methods and apparatus disclosed herein may be made without departing form the scope of the instant disclosure, which is defined in the appended claims. The words "including" and "having," as used herein and including the claims, shall have the same meaning as the word "comprising."

What is claimed is:

1. A catheter comprising:
an elongated catheter body including a proximal end and a distal end, the body defining a plurality of lumens;
a plurality of extension tubes, each of the plurality of extension tubes comprising a lumen in fluid communication with one lumen of the plurality of lumens of the catheter body;
a selection valve element coupled to two or more of the plurality of extension tubes such that the selection valve element can selectively allow fluid communication through a first extension tube of the two or more of the plurality of extension tubes while preventing fluid communication through a second extension tube of the two or more of the plurality of extension tubes and selectively allow fluid communication through the second extension tube while preventing fluid communication through the first extension tube; and
wherein at least one of the plurality of extension tubes is capable of performing power injection at about 300 psi, and at least one of the plurality of extension tubes includes a proximal two-way pressure activated valve.

2. The catheter of claim 1, wherein the proximal valve is configured to:
allow infusion when an infusion pressure differential exceeds a selected magnitude; and
allow aspiration when an aspiration pressure differential exceeds a selected magnitude.

3. The catheter of claim 1, further comprising a pressure relief mechanism configured to prevent overpressurizing at least one of the plurality of lumens of the catheter body, the pressure relief mechanism comprising one or more of the following: a balloon, a burst disk, a relief valve, or an inline valve.

4. The catheter of claim 1, wherein the catheter is configured to accommodate a fluid flow rate of at least about 5 cc per second through the plurality of lumens.

5. The catheter of claim 1, wherein the catheter is designed to maintain high internal pressure associated with power injection, but release pressure through the proximal two-way pressure activated valve before the catheter body would rupture due to overpressurization.

6. The catheter of claim 1, wherein the selection valve element operates automatically to selectively allow fluid communication through either the first extension tube or the second extension tube.

7. The catheter of claim 1, wherein the selection valve element includes a shuttle element that selectively allows fluid communication through either the first extension tube or the second extension tube, while preventing fluid communication through at least one other extension tube of the plurality of extension tubes.

8. The catheter of claim 1, wherein the at least one of the plurality of extension tubes is capable of performing power injection at about 400 psi.

9. The catheter of claim 1, wherein:
the plurality of lumens comprises a first lumen and a second lumen; and
the plurality of extension tubes comprises:
a main extension tube in fluid communication with the first lumen; and
two secondary extension tubes configured for fluid communication with the second lumen.

10. The catheter of claim 9, wherein the main extension tube further comprises a connector to which the first of the two secondary extension tubes may be coupled so that fluid communication may occur with the first lumen and the second lumen of the catheter simultaneously.

11. The catheter of claim 9, wherein a first of the two secondary extension tubes is configured for performing power injection and a second of the two secondary extension tubes includes the proximal valve.

12. The catheter of claim 11, further comprising:
a valve for controlling fluid communication between the second lumen of the catheter body and one of the following: the first of the two secondary extension tubes configured for performing power injection or the second of the two secondary extension tubes including the proximal valve.

13. The catheter of claim 1, wherein:
the body of the catheter defines a first lumen, a second lumen, and a third lumen; and
the plurality of extension tubes comprises:
a main extension tube in fluid communication with the first lumen of the catheter;
a first pair of secondary extension tubes configured for fluid communication with the second lumen of the catheter; and
a second pair of secondary extension tubes configured for fluid communication with the third lumen of the catheter.

14. The catheter of claim 13, wherein the main extension tube further comprises a connector to which a first of the first pair of secondary extension tubes and a first of the second pair of extension tubes may be coupled so that fluid communication may occur with each of the first lumen, second lumen, and third lumen of the catheter simultaneously.

15. The catheter of claim 13, wherein:
a first of the first pair of secondary extension tubes and a first of the second pair of secondary extension tubes are configured for performing power injection; and
a second of the first pair of secondary extension tubes and a second of the second pair of secondary extension tubes include a proximal valve.

16. The catheter of claim 15, further comprising:
a first valve for controlling fluid communication between the second lumen of the catheter body and one of the following: the first of the first pair of secondary extension tubes configured for performing power injection or the second of the first pair of secondary extension tubes including the proximal valve; and
a second valve for controlling fluid communication between the third lumen of the catheter body and one of the following: the first of the second pair of secondary extension tubes configured for performing power injection or the second of the second pair of secondary extension tubes including the proximal valve.

17. The catheter of claim 1, wherein the proximal valve comprises a deformable element including a slit formed through the deformable element.

18. The catheter of claim 17, wherein the deformable element comprises a deformable disk positioned between a proximal body portion and a distal body portion of the proximal valve.

19. The catheter of claim 18, wherein the proximal body portion and the distal body portion are affixed to one another.

20. The catheter of claim 17, further comprising a cap affixable to the at least one of the plurality of extension tubes including the proximal valve, the cap configured to inhibit fluid communication through the at least one of the plurality of extension tubes including the proximal valve.

21. The catheter of claim 20, wherein the cap further comprises a support element extending from a distal end of cap, the support element configured to contact the deformable element and resist fluid communication through the deformable element.

* * * * *